United States Patent
Palakodety et al.

(10) Patent No.: US 12,254,112 B2
(45) Date of Patent: Mar. 18, 2025

(54) METHODS AND SYSTEMS FOR CRYPTOGRAPHICALLY SECURED DECENTRALIZED TESTING

(71) Applicant: Onai, Inc., San Jose, CA (US)

(72) Inventors: Shriphani Palakodety, San Jose, CA (US); Volkmar Frinken, San Jose, CA (US); Patrick Grinaway, Brooklyn, NY (US); Galana Gebisa, Mountain View, CA (US); Guha Jayachandran, Cupertino, CA (US)

(73) Assignee: Onai Inc., San Jose, CA (US)

( * ) Notice: Subject to any disclaimer, the term of this patent is extended or adjusted under 35 U.S.C. 154(b) by 251 days.

(21) Appl. No.: 17/858,513

(22) Filed: Jul. 6, 2022

(65) Prior Publication Data

US 2022/0358241 A1    Nov. 10, 2022

Related U.S. Application Data

(63) Continuation-in-part of application No. 17/140,474, filed on Jan. 4, 2021, now Pat. No. 11,409,907, which is a continuation-in-part of application No. 16/884,460, filed on May 27, 2020, now Pat. No. 10,887,104.

(60) Provisional application No. 63/003,810, filed on Apr. 1, 2020.

(51) Int. Cl.
*G06F 21/62* (2013.01)
*H04L 9/32* (2006.01)

(52) U.S. Cl.
CPC ........ *G06F 21/6245* (2013.01); *H04L 9/3218* (2013.01); *H04L 9/3247* (2013.01)

(58) Field of Classification Search
CPC .. G06F 21/6245; H04L 9/3247; H04L 9/3218
See application file for complete search history.

(56) References Cited

U.S. PATENT DOCUMENTS

| | | | | |
|---|---|---|---|---|
| 8,549,310 | B2 * | 10/2013 | Walker | H04L 9/3218 713/168 |
| 9,710,636 | B1 * | 7/2017 | Redpath | G06K 19/07749 |
| 9,747,653 | B2 * | 8/2017 | Haider | G06Q 10/06 |
| 10,298,395 | B1 | 5/2019 | Schiatti | |
| 10,298,404 | B1 * | 5/2019 | Behm | H04L 9/3247 |
| 10,491,390 | B2 | 11/2019 | Gurkan | |

(Continued)

FOREIGN PATENT DOCUMENTS

| WO | WO2019179538 | 9/2019 |
|---|---|---|
| WO | WO2019228550 | 12/2019 |

OTHER PUBLICATIONS https://medium.com/blockwhat/merkle-trees-ensuring-integrity-on-blockchains-508d6647d58e Title: Merkle Trees—Ensuring Integrity on Blockchains Date: Dec. 26, 2018 By: Till Antonio Mahler.

(Continued)

*Primary Examiner* — Viral S Lakhia
(74) *Attorney, Agent, or Firm* — Caldwell Intellectual Property Law

(57) ABSTRACT

A method of cryptographically secured decentralized testing includes receiving, by a computing device and from a secure test apparatus, an output of a cryptographic function of a secret test result identifier, authenticating the output, and recording, in a data repository, an indication of a test result as a function of the output.

20 Claims, 10 Drawing Sheets

(56) References Cited

U.S. PATENT DOCUMENTS

| | | | |
|---|---|---|---|
| 10,636,527 B2* | 4/2020 | Pulitzer | G16H 80/00 |
| 10,742,421 B1* | 8/2020 | Wentz | H04L 9/0897 |
| 10,949,558 B2* | 3/2021 | Dunaway | G06F 21/602 |
| 11,010,754 B2* | 5/2021 | Campero | G06F 17/142 |
| 11,055,390 B1* | 7/2021 | Kragh | H04L 9/3297 |
| 11,088,851 B2* | 8/2021 | Shamai | H04L 63/1441 |
| 11,095,446 B2* | 8/2021 | Monica | H04L 9/0822 |
| 11,316,692 B2* | 4/2022 | Wentz | H04L 9/3221 |
| 11,379,263 B2* | 7/2022 | Wentz | H04L 9/3221 |
| 11,769,585 B2* | 9/2023 | Youngblood | G16H 20/60 |
| | | | 705/3 |
| 2017/0264428 A1 | 9/2017 | Seger, II | |
| 2018/0052958 A1* | 2/2018 | Crawford | G16H 40/63 |
| 2018/0102903 A1* | 4/2018 | Kipnis | H04L 9/3247 |
| 2018/0323974 A1 | 11/2018 | Gao et al. | |
| 2019/0147438 A1 | 5/2019 | Micali | |
| 2019/0182047 A1 | 6/2019 | Andreina et al. | |
| 2019/0278758 A1 | 9/2019 | Zhang et al. | |
| 2019/0296916 A1 | 9/2019 | Qiu | |
| 2019/0303623 A1* | 10/2019 | Reddy | G06F 8/71 |
| 2019/0356674 A1 | 11/2019 | Irazabal et al. | |
| 2019/0370250 A1 | 12/2019 | Tipton et al. | |
| 2020/0177397 A1* | 6/2020 | Harrington | H04L 9/3297 |

OTHER PUBLICATIONS https://www.networkworld.com/article/3390722/how-data-storage-will-shift-to-blockchain.html Title: How Data Storage Will Shift to Blockchain Date: Apr. 24, 2019 By: Patrick Nelson.
https://coincentral.com/merkle-tree-hashing-blockchain/ Title: How You Make a Merkle Tree Date: Sep. 3, 2018 By: Bennett Garner.

* cited by examiner

METHODS AND SYSTEMS FOR CRYPTOGRAPHICALLY SECURED DECENTRALIZED TESTING

CROSS-REFERENCE TO RELATED APPLICATIONS

This application is a continuation-in-part of U.S. Nonprovisional application Ser. No. 17/140,474 filed on Jan. 4, 2021 and entitled "METHODS AND SYSTEMS FOR CRYPTOGRAPHICALLY SECURED DECENTRALIZED TESTING," which is a continuation-in-part of U.S. Nonprovisional application Ser. No. 16/884,460, dated May 27, 2020, and entitled "METHODS AND SYSTEMS FOR CRYPTOGRAPHICALLY SECURED DECENTRALIZED TESTING," which claims the benefit of priority of U.S. Provisional Patent Application Ser. No. 63/003,810, filed on Apr. 1, 2020, and titled "METHODS AND SYSTEMS FOR CRYPTOGRAPHICALLY SECURED DECENTRALIZED TESTING." Each of U.S. Nonprovisional application Ser. No. 17/140,474, U.S. Nonprovisional application Ser. No. 16/884,460, and U.S. Provisional Patent Application Ser. No. 63/003,810 is incorporated by reference herein in its entirety.

FIELD OF THE INVENTION

The present invention generally relates to the field of diagnostic devices and systems. In particular, the present invention is directed to methods and systems for cryptographically secured decentralized testing.

BACKGROUND

In many situations, it is useful for disparate individuals to conduct a test, medical or otherwise, and report the results to a database, blockchain, or other data store. As one example, it may be desired for individuals to perform serological tests to show whether they have developed immunity to a virus and report this information. Or it may be desired for individuals to perform a nucleic acid test to determine if they are currently infected by a virus and report this in order for others who had recently been near them to know that they may have been exposed to the virus.

If anyone is allowed to report results, then the danger is that individuals may report false results, with various undesirable consequences. One may therefore require a designated trusted party, such as a governmental authority, to certify a test result. However, this requires the involvement of the trusted party to participate in the performance of every test.

SUMMARY OF THE DISCLOSURE

In an aspect, a method of cryptographically secured medical testing includes capturing, by a computing device, an unsealed test identifier corresponding to a test apparatus, generating, by the computing device, a cryptographic commitment to the unsealed test identifier, recording, by the computing device, a test result from the test apparatus, transmitting, by the computing device, to at least a local device a message including the test result, receiving, by the computing device, a digital signature on the message from the at least a local device, and generating, by the computing device, a record, the record including the digitally signed message and a secure proof of the commitment.

In another aspect, a non-transitory memory containing instructions configuring at least a processor to perform method steps for cryptographically secured medical testing, the method steps including capturing an unsealed test identifier corresponding to a test apparatus, generating a cryptographic commitment to the unsealed test identifier, recording a test result from the test apparatus, transmitting to at least a local device a message including the test result, receiving a digital signature on the message from the at least a local device, and generating a record, the record including the digitally signed message and a secure proof of the commitment.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
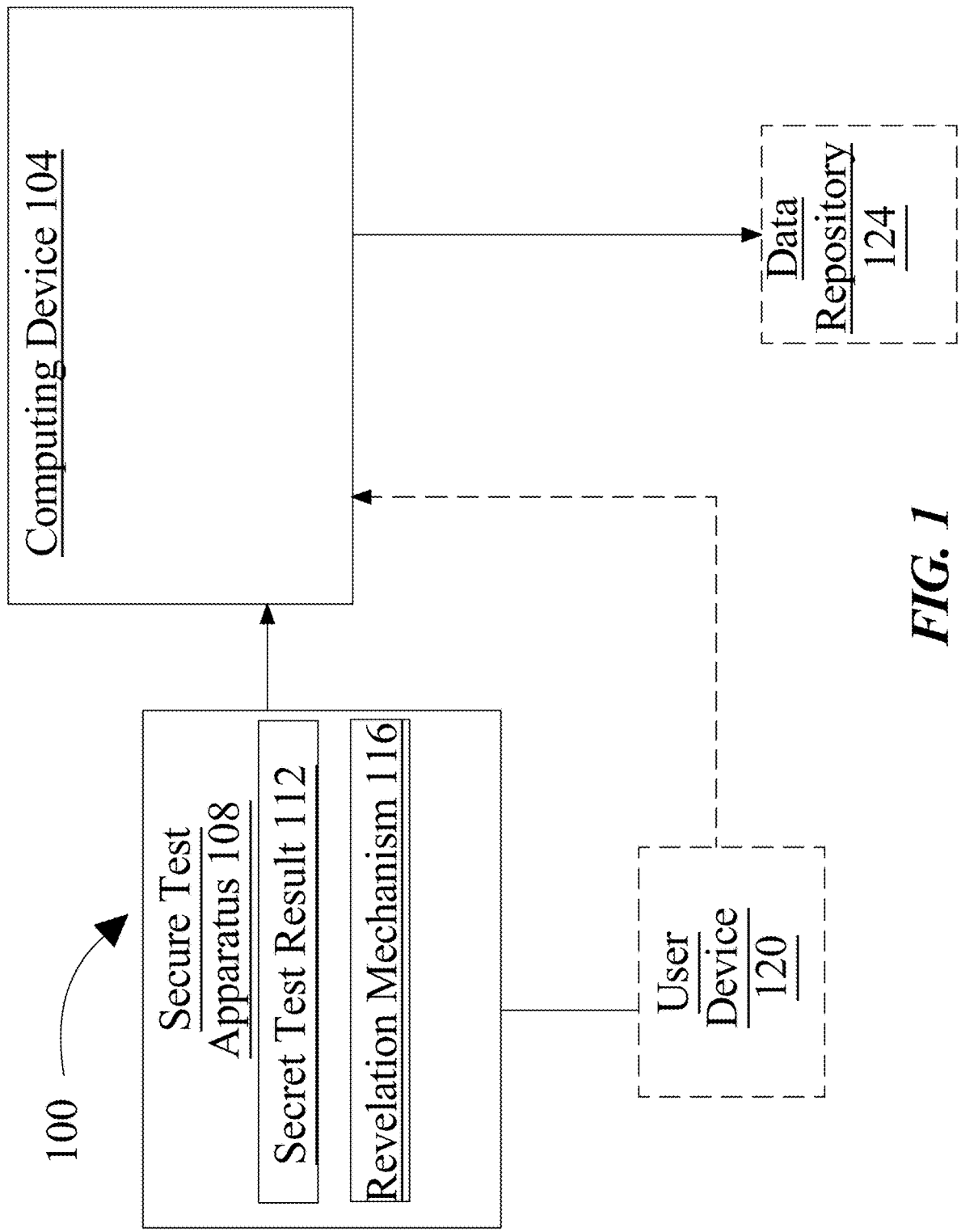
FIG. 1 is a block diagram illustrating an exemplary embodiment of a system for cryptographically secured decentralized testing.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments disclosed herein allow decentralized testing, with authenticatable results, without the involvement of a trusted authority in the performance of the test. Some embodiments of disclosed methods entail a use of a test apparatus that has been pre-bundled with a unique identifier (such as a barcode for example), with this identifier only exposed when there is a particular test result. An individual may be unable to predict an identifier ahead of time, prior to a test result being obtained. After a test, software executed by a testing device and/or a program operating on a user device may compute a cryptographic function of the exposed identifier and then report the test result and/or computed value to a data store, such as a designated database or blockchain. In an embodiment, a trusted party that issued a test may have prior to issuance of tests committed data (optionally as a cryptographic accumulator) to a public data store, committing to the identifiers it is issuing, such that the tested party can later construct a proof that an identifier, or cryptographic function thereof, was indeed previously committed by the issuing authority, such proof verifiable by anyone. In another embodiment, an issuing authority may confirm an identifier after it is sent from the tested party.

In this manner, even though an issuing trusted party was not involved performing the test, it and/or other parties may be able to confirm that a test was authentic, and that a given result was indeed obtained because it is impossible, or difficult enough to be practically infeasible, for the tested party to have known the identifier to compute and report a cryptographic function of that identifier unless there was in fact a test performed. A trusted party or any observing party may impose additional safeguards such as accepting a report of a given identifier only once or imposing various time constraints on reporting.

In an embodiment, methods and systems described herein may perform or implement one or more aspects of a cryptographic system. In one embodiment, a cryptographic system is a system that converts data from a first form, known as "plaintext," which is intelligible when viewed in its intended format, into a second form, known as "ciphertext," which is not intelligible when viewed in the same way. Ciphertext may be unintelligible in any format unless first converted back to plaintext. In one embodiment, a process of converting plaintext into ciphertext is known as "encryption." Encryption may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

In embodiments of cryptographic systems that are "asymmetric," either encryption or decryption key cannot be readily deduced without additional secret knowledge, even given the possession of a corresponding decryption or encryption key, respectively; a common example is a "public key cryptographic system," in which possession of the encryption key does not make it practically feasible to deduce the decryption key, so that the encryption key may safely be made available to the public. An example of a public key cryptographic system is RSA, in which an encryption key involves the use of numbers that are products of very large prime numbers, but a decryption key involves the use of those very large prime numbers, such that deducing the decryption key from the encryption key requires the practically infeasible task of computing the prime factors of a number which is the product of two very large prime numbers. A further example of an asymmetric cryptographic system may include a discrete-logarithm based system based upon the relative ease of computing exponents mod a large integer, and the computational infeasibility of determining the discrete logarithm of resulting numbers absent previous knowledge of the exponentiations; an example of such a system may include Diffie-Hellman key exchange and/or public key encryption. Another example is elliptic curve cryptography, which relies on the fact that given two points P and Q on an elliptic curve over a finite field, a definition of the inverse of a point −A as the point with negative y-coordinates, and a definition for addition where A+B=−R, the point where a line connecting point A and point B intersects the elliptic curve, where "0," the identity, is a point at infinity in a projective plane containing the elliptic curve, finding a number k such that adding P to itself k times results in Q is computationally impractical, given correctly selected elliptic curve, finite field, and P and Q. A further example of asymmetrical cryptography may include lattice-based cryptography, which relies on the fact that various properties of sets of integer combination of basis vectors are hard to compute, such as finding the one combination of basis vectors that results in the smallest Euclidean distance. Embodiments of cryptography, whether symmetrical or asymmetrical, may include quantum-secure cryptography, defined for the purposes of this disclosure as cryptography that remains secure against adversaries possessing quantum computers; some forms of lattice-based cryptography, for instance, may be quantum-secure.

Embodiments of systems and methods described herein may generate, evaluate, and/or utilize digital signatures. A "digital signature," as used herein, includes a secure proof of possession of a secret by a signing device, as performed on a provided element of data, known as a "message." A message may include an encrypted mathematical representation of a file or other set of data using the private key of a public key cryptographic system. Secure proof may include any form of secure proof as described in further detail below, including without limitation encryption using a private key of a public key cryptographic system as described above. Signature may be verified using a verification datum suitable for verification of a secure proof; for instance, where secure proof is enacted by encrypting message using a private key of a public key cryptographic system, verification may include decrypting the encrypted message using the corresponding public key and comparing the decrypted representation to a purported match that was not encrypted; if the signature protocol is well-designed and implemented correctly, this means the ability to create the digital signature is equivalent to possession of the private decryption key and/or device-specific secret. Likewise, if a message making up a mathematical representation of file is well-designed and implemented correctly, any alteration of the file may result in a mismatch with the digital signature; the mathematical representation may be produced using an alteration-sensitive, reliably reproducible algorithm, such as a hashing algorithm as described above. A mathematical representation to which the signature may be compared may be included with signature, for verification purposes; in other embodiments, the algorithm used to produce the mathematical representation may be publicly available, permitting the easy reproduction of the mathematical representation corresponding to any file.

In some embodiments, digital signatures may be combined with or incorporated in digital certificates. In one embodiment, a digital certificate is a file that conveys information and links the conveyed information to a "certificate authority" that is the issuer of a public key in a public key cryptographic system. Certificate authority in some embodiments contains data conveying the certificate authority's authorization for the recipient to perform a task. The authorization may be the authorization to access a given datum. The authorization may be the authorization to access a given process. In some embodiments, the certificate may identify the certificate authority. The digital certificate may include a digital signature.

In some embodiments, a third party such as a certificate authority (CA) is available to verify that the possessor of the private key is a particular entity; thus, if the certificate authority may be trusted, and the private key has not been stolen, the ability of an entity to produce a digital signature confirms the identity of the entity and links the file to the entity in a verifiable way. Digital signature may be incorporated in a digital certificate, which is a document authenticating the entity possessing the private key by authority of the issuing certificate authority and signed with a digital signature created with that private key and a mathematical representation of the remainder of the certificate. In other embodiments, digital signature is verified by comparing the digital signature to one known to have been created by the entity that purportedly signed the digital signature; for instance, if the public key that decrypts the known signature also decrypts the digital signature, the digital signature may be considered verified. Digital signature may also be used to verify that the file has not been altered since the formation of the digital signature.

Referring now to FIG. 1, an exemplary embodiment of a system 100 for cryptographically secured decentralized testing is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may communicate with a secure test apparatus 108. A "secure test apparatus 108," as used in this disclosure, is a device that generates an output upon detection of a chemical agent, such as without limitation a biochemical marker or biomarker such as a marker indicative of a given medical condition, such as without limitation a viral, bacterial, protist, and/or fungal infection; such detection may be referred to for purposes of this disclosure as a "positive result." As a non-limiting example, medical condition may include Coronavirus disease 2019 (COVID 19) caused by one or more variants of severe acute respiratory syndrome coronavirus 2 (SARS-CoV-2), or similar conditions. In general, secure test apparatus 108 may test for presence and/or threshold levels of any chemical in any suspension, solution and/or other material or mixture of materials, using any means or method for such detection, including without limitation testing water for presence and/or levels of any chemical. Secure test apparatus 108 may alternatively or additionally test for particulate matter in suspension, for microorganisms, degree of turbidity, or the like. Secure test apparatus 108 may include a concealed secret test result 112, defined for the purposes of this disclosure as a datum that is stored in or on secure test apparatus in a manner that is undetectable to users or other devices prior to a positive result. Secure test apparatus 108 may include a positive result detection mechanism, which is defined for the purposes of this disclosure as any mechanism designed and configured to reveal the secret test result 112 upon detecting a positive result for a medical condition and/or other chemical or other substance and/or quality as described above. Revelation mechanism 115 may include a chemical revelation mechanism 115. For instance, a manufacturer or other issuing party may pre-print a unique identifier on each test strip the issuing party issues. Unique identifier may include textual information such as an alphanumeric and/or numeric string; alternatively or additionally, unique identifier may be encoded using a visually scannable pattern such as a barcode, a quick read (QR) code, or the like; unique identifier may be unique within system 100 and/or any set of devices and/or systems in communication with system, and/or may be a statistically unique identifier as determined for instance according to globally unique identifier (GUID) and/or universally unique identifier (UUID) protocols. Identifier may be deposited upon or within a physical substrate such as a test strip as an invisible mask on the test strip's positive signal stripe and/or other pattern that changes color upon exposure to a chemical, such as without limitation a biomarker, as described above, or it may be that the positive signal stripe is itself printed in the pattern of a unique barcode or other identifier. Unique identifier may thus only be exposed when there is a positive test. Concealed test result may include a steganographically concealed secret test result 112.

Alternatively or additionally, and still referring to FIG. 1, positive result detection mechanism may include a digital testing device, which may directly detect a chemical, biomarker, or other element as described above, and/or a chemical reaction of biomarker or other chemical with an antigen or other chemical agent by measuring an alteration of an electronic parameter such as voltage, current, capacitance, inductance, or the like, and/or by optically scanning a test strip or other substrate having a visible indicia thereon containing a unique ID; unique ID may alternatively or additionally be hardcoded and/or otherwise stored in circuitry of secure test apparatus 108. Such circuitry may be tamper proof; for instance, circuitry may be disabled and/or denatured by attempted tampering, and/or may contain elements that detect tampering attempts. Positive result detection mechanism and/or secure test apparatus 108 may include a digital display of unique identifier, in any form as described above when a positive test is detected. Alternatively or additionally, unique identifier and/or an output of a cryptographic function thereof, as described in further detail below, may be generated by circuitry of secure test apparatus 108. Alternatively, tamper-proofing may be achieved with a chemical revelation mechanism that is difficult to duplicate.

Further referring to FIG. 1, secret test result 112 may be encoded using error correction codes. An error correction code, also known as error correcting code (ECC), is an encoding of a message or lot of data using redundant information, permitting recovery of corrupted data. An ECC may include a block code, in which information is encoded on fixed-size packets and/or blocks of data elements such as symbols of predetermined size, bits, or the like. Reed-Solomon coding, in which message symbols within a symbol set having q symbols are encoded as coefficients of a polynomial of degree less than or equal to a natural number k, over a finite field F with q elements; strings so encoded have a minimum hamming distance of k+1, and permit correction of (q−k−1)/2 erroneous symbols. Block code may alternatively or additionally be implemented using Golay coding, also known as binary Golay coding, Bose-Chaudhuri, Hocquenghuem (BCH) coding, multidimensional parity-check coding, and/or Hamming codes. An ECC may alternatively or additionally be based on a convolutional code.

In an embodiment, and still referring to FIG. 1, use of ECC in secret test result 112 may enable secret test result 112 to be scanned, read, evaluated, and/or verified according to any process described in this disclosure, even if secret test result 112 has been occluded, damaged, and/or subjected to one or more sources of noise and/or data corruption.

With continued reference to FIG. 1, where secure test apparatus 108 displays unique identifier or any other output of positive result detection mechanism, whether digitally or in the form of visible indicia on a substrate, computing device 104 may receive a communication based on secret test identifier, which may be any identifier and/or unique identifier as described above. User device 120 may scan display using a camera or other optical capture device. User device 120 may alternatively scan a visible display of cryptographic function output as described below. Alternatively or additionally, where secure test apparatus 108 includes electronic circuitry, such circuitry may transmit secret test result identifier and/or an output of a cryptographic function as described below to user device 120. User device 120 and/or secure test apparatus 108 may transmit output of cryptographic function, and/or secret test result identifier to computing device 104 over any electronic communication network as described in this disclosure. User device 120 may be configured by computing device 104 to perform any steps as described herein, for instance via a client-side program transmitted as part of a web application, and/or by a native application such as a mobile "app" transmitted to and/or stored on user device 120.

Still referring to FIG. 1, secure test apparatus 108 and/or user device 120 may be configured to generate and/or transmit to computing device 104 an output of a cryptographic function of a secret test result identifier. A "cryptographic function" of secret test result identifier, as used in this disclosure, is any function that generates an output that may be conclusively linked via proof or verification to secret test result identifier, but from which it is impossible and/or computationally infeasible to discover secret test result identifier. In an embodiment, cryptographic function may produce a cryptographic hash, also referred to by the equivalent shorthand term "hash," of secret test result identifier. A cryptographic hash, as used herein, is a mathematical representation of a lot of data, such as files or blocks in a blockchain as described in further detail below; the mathematical representation is produced by a lossy "one-way" algorithm known as a "hashing algorithm." Hashing algorithm may be a repeatable process; that is, identical lots of data may produce identical hashes each time they are subjected to a particular hashing algorithm. Because hashing algorithm is a one-way function, it may be impossible to reconstruct a lot of data from a hash produced from the lot of data using the hashing algorithm. In the case of some hashing algorithms, reconstructing the full lot of data from the corresponding hash using a partial set of data from the full lot of data may be possible only by repeatedly guessing at the remaining data and repeating the hashing algorithm; it is thus computationally difficult if not infeasible for a single computer to produce the lot of data, as the statistical likelihood of correctly guessing the missing data may be extremely low. However, the statistical likelihood of a computer of a set of computers simultaneously attempting to guess the missing data within a useful timeframe may be higher, permitting mining protocols as described in further detail below.

In an embodiment, and continuing to refer to FIG. 1, hashing algorithm may demonstrate an "avalanche effect," whereby even extremely small changes to lot of data produce drastically different hashes. This may thwart attempts to avoid the computational work necessary to recreate a hash by simply inserting a fraudulent datum in data lot, enabling the use of hashing algorithms for "tamper-proofing" data such as data contained in an immutable ledger as described in further detail below. This avalanche or "cascade" effect may be evinced by various hashing processes; persons skilled in the art, upon reading the entirety of this disclosure, will be aware of various suitable hashing algorithms for purposes described herein. Verification of a hash corresponding to a lot of data may be performed by running the lot of data through a hashing algorithm used to produce the hash. Such verification may be computationally expensive, albeit feasible, potentially adding up to significant processing delays where repeated hashing, or hashing of large quantities of data, is required, for instance as described in further detail below. Examples of hashing programs include, without limitation, SHA 256, a NIST standard; further current and past hashing algorithms include Winternitz hashing algorithms, various generations of Secure Hash Algorithm (including "SHA-1," "SHA-2," and "SHA-3"), "Message Digest" family hashes such as "MD4," "MD5," "MD6," and "RIPEMD," Keccak, "BLAKE" hashes and progeny (e.g., "BLAKE2," "BLAKE-256," "BLAKE-512," and the like), Message Authentication Code ("MAC")—family hash functions such as PMAC, OMAC, VMAC, HMAC, and UMAC, Poly 1305-AES, Elliptic Curve Only Hash ("ECOH") and similar hash functions, Fast-Syndrome-based (FSB) hash functions, GOST hash functions, the Grøstl hash function, the HAS-160 hash function, the JH hash function, the RadioGatún hash function, the Skein hash function, the Streebog hash function, the SWIFFT hash function, the Tiger hash function, the Whirlpool hash function, or any hash function that satisfies, at the time of implementation, the requirements that a cryptographic hash be deterministic, infeasible to reverse-hash, infeasible to find collisions, and have the property that small changes to an original message to be hashed will change the resulting hash so extensively that the original hash and the new hash appear uncorrelated to each other. A degree of security of a hash function in practice may depend both on the hash function itself and on characteristics of the message and/or digest used in the hash function. For example, where a message is random, for a hash function that fulfills collision-resistance requirements, a brute-force or "birthday attack" may to detect collision may be on the order of $O(2^{n/2})$ for n output bits; thus, it may take on the order of $2^{256}$ operations to locate a collision in a 512 bit output "Dictionary" attacks on hashes likely to have been generated from a non-random original text can have a lower computational complexity, because the space of entries they are guessing is far smaller than the space containing all random permutations of bits. However, the space of possible messages may be augmented by increasing the length or potential length of a possible message, or by implementing a protocol whereby one or more randomly selected strings or sets of data are added to the message, rendering a dictionary attack significantly less effective.

Alternatively or additionally, and still referring to FIG. 1, output of cryptographic function may include a secure proof of possession of secret test result 112. A secure proof, as used herein, is a protocol whereby an output is generated that demonstrates possession of a secret, such as a secret test result identifier, without demonstrating the entirety of the secret; in other words, a secure proof by itself, is insufficient to reconstruct the entire secret, enabling the production of at least another secure proof using at least a secret. Where at least a secret is a plurality of secrets, such as a plurality of challenge-response pairs, a secure proof may include an output that reveals the entirety of one of the plurality of secrets, but not all of the plurality of secrets; for instance, secure proof may be a response contained in one challenge-response pair. In an embodiment, proof may not be secure; in other words, proof may include a one-time revelation of at least a secret, for instance as used in a single challenge-response exchange.

Still referring to FIG. 1, secure proof may include a zero-knowledge proof, which may provide an output demonstrating possession of a secret while revealing none of the secret to a recipient of the output. Zero-knowledge proof may be information-theoretically secure, meaning that an entity with infinite computing power would be unable to determine secret from output. Alternatively, zero-knowledge proof may be computationally secure, meaning that determination of secret from output is computationally infeasible, for instance to the same extent that determination of a private key from a public key in a public key cryptographic system is computationally infeasible. Zero-knowledge proof algorithms may generally include a set of two algorithms, a prover algorithm, or "P," which is used to prove computational integrity and/or possession of a secret, and a verifier algorithm, or "V" whereby a party may check the validity of P. Zero-knowledge proof may include an interactive zero-knowledge proof, wherein a party verifying the proof must directly interact with the proving party; for instance, the verifying and proving parties may be required to be online, or connected to the same network as each other, at the same time. Interactive zero-knowledge proof may include a "proof of knowledge" proof, such as a Schnorr algorithm for proof of knowledge of a discrete logarithm. in a Schnorr algorithm, a prover commits to a randomness r, generates a message based on r, and generates a message adding r to a challenge c multiplied by a discrete logarithm that the prover is able to calculate; verification is performed by the verifier who produced c by exponentiation, thus checking the validity of the discrete logarithm. Interactive zero-knowledge proofs may alternatively or additionally include sigma protocols. Persons skilled in the art, upon reviewing the entirety of this disclosure, will be aware of various alternative interactive zero-knowledge proofs that may be implemented consistently with this disclosure.

Alternatively, and still referring to FIG. 1, zero-knowledge proof may include a non-interactive zero-knowledge, proof, or a proof wherein neither party to the proof interacts with the other party to the proof; for instance, each of a party receiving the proof and a party providing the proof may receive a reference datum which the party providing the proof may modify or otherwise use to perform the proof. As a non-limiting example, zero-knowledge proof may include a succinct non-interactive arguments of knowledge (ZK-SNARKS) proof, wherein a "trusted setup" process creates proof and verification keys using secret (and subsequently discarded) information encoded using a public key cryptographic system, a prover runs a proving algorithm using the proving key and secret information available to the prover, and a verifier checks the proof using the verification key; public key cryptographic system may include RSA, elliptic curve cryptography, ElGamal, or any other suitable public key cryptographic system. Generation of trusted setup may be performed using a secure multiparty computation so that no one party has control of the totality of the secret information used in the trusted setup; as a result, if any one party generating the trusted setup is trustworthy, the secret information may be unrecoverable by malicious parties. As another non-limiting example, non-interactive zero-knowledge proof may include a Succinct Transparent Arguments of Knowledge (ZK-STARKS) zero-knowledge proof. In an embodiment, a ZK-STARKS proof includes a Merkle root of a Merkle tree representing evaluation of a secret computation at some number of points, which may be 1 billion points, plus Merkle branches representing evaluations at a set of randomly selected points of the number of points; verification may include determining that Merkle branches provided match the Merkle root, and that point verifications at those branches represent valid values, where validity is shown by demonstrating that all values belong to the same polynomial created by transforming the secret computation. In an embodiment, ZK-STARKS does not require a trusted setup. ZK-STARKS may not rely on private-public key pairings but may rely on collision resistant hashing and a random oracle model. Collision resistant hashing may be measured if it is hard to find two inputs that hash to the same output, which is two inputs such as a and b such that $H(a)=H(b)$, and $a \neq b$. Collision resistant hash functions may include a strong one-way hash function. ZK-STARKS may utilize collision-resistant hash functions to convert a STIK into an interactive argument of knowledge system, whereby a STIK is defined as a Scalable Transparent Interactive Oracle Proof of Knowledge. A ZK-STIK may be proven to be unconditionally sound, even against computationally unbounded provers. If the STIK has perfect ZK, then the argument system has computational ZK. Any realization of a STIK using this technique may be considered interactive. Collision resistance may be desirable for example, when a party may attest to a document by publishing a public key signature on a hash of the document. A malicious actor may be able to get a party to attest to one document and then produce another document copying that attestation thereby producing the same hash and claiming the other party had attested to both documents. Collision resistance hashing may also be employed for example when parties may compare cryptographic of a file to make sure they both have the same version. A bad actor could produce two files each containing the same hash and trick users into believing they had the same version of a file when in fact they did not. ZK-STARKS may also utilize a random oracle model. Random oracle output may include an output that responds to every unique query with a truly random or pseudorandom response chosen uniformly or preferentially from its output domain; in an embodiment, a pseudorandom output is one that is infeasible to predict prior to performing steps of random oracle, such as without limitation an output including an output of a cryptographic hash function performed on each unique query. If a query is repeated the output may respond the same way every time that query is submitted. In an embodiment, a random oracle output may include a mathematical function chosen uniformly at random, so that each possible query has an output of a fixed random response. A random oracle may include a verifiable delay function, e.g. a function based on exponentiation in a group of unknown order, a verifiable random function as demonstrated by DFINITY of Zug, Switzerland, a random beacon, such as without limitation a high entropy source such as true random number generator (TRNG) that is signed and time-stamped by a device with trusted properties. Using the random oracle model any STIK can be compiled into a non-interactive argument of knowledge in the random oracle knowledge. If the STIK has perfect ZK then the resulting construction has computational zero knowledge. Realization of a STIK using this technique may be considered non-interactive STARK. Decisions as to whether to use interactive or non-interactive ZK-STARKS may be determined by requesting device 104 and/or system designer.

With continued reference to FIG. 1, zero-knowledge proof may include any other suitable zero-knowledge proof. Zero-knowledge proof may include, without limitation bulletproofs. Zero-knowledge proof may include a homomorphic public-key cryptography (hPKC)-based proof. Zero-knowledge proof may include a discrete logarithmic problem (DLP) proof. Zero-knowledge proof may include a secure multi-party computation (MPC) proof. Zero-knowledge proof may include, without limitation, an incrementally verifiable computation (IVC). Zero-knowledge proof may include an interactive oracle proof (IOP). Zero-knowledge proof may include a proof based on the probabilistically checkable proof (PCP) theorem, including a linear PCP (LPCP) proof. Persons skilled in the art, upon reviewing the entirety of this disclosure, will be aware of various forms of zero-knowledge proofs that may be used, singly or in combination, consistently with this disclosure.

Still referring to FIG. 1, cryptographic function may be performed using one or more privacy-preserving protocols. A "privacy-preserving protocol," as used in this disclosure, is a protocol that makes it impossible or computationally infeasible to determine an identity of a party performing a test, who may be referred to as a "tester" for the purposes of this disclosure, given an output of the cryptographic function. As a non-limiting example, where a test issuer distributes test kits, tester may be able to publicly report and prove the validity of a result using a privacy-preserving protocol, without the test issuer being able to map that result to a given tester, even if the test issuer has kept track of which test kit (with what code) it issued to what tester. In an embodiment, privacy-preserving protocol may include participation by test issuer and/or operator of computing device 104 or other device operated by a test issuer (any of which may be referred to for the purposes of discussion of this discussion of privacy-preserving protocols as a "test issuer") and one or more testers and/or devices operated thereby, including without limitation a secure test apparatus 108, and/or user device, where tester and/or device operated thereby may be referred to for the sake of discussion of privacy-preserving protocols as the tester, in a set of intercommunications, exchanges of information, and/or instantiation and/or evaluation of cryptographic objects and/or primitives to enact privacy-preserving protocol. In an exemplary embodiment, a test issuer, prior to any testing, may publish to data store, including without limitation an immutable sequential listing and/or any data store described in this disclosure, a cryptographic commitment as defined below to a set of all potential exposed secret test result identifiers across all tests. Non-limiting examples of cryptographic commitments are Pedersen commitments and Fujisaki-Okamoto commitments. Using a one-out-of-many cryptographic proof a tester may issue a proof that it knows one of those codes without revealing which of them it knows. As a non-limiting example, a one-of-many proof may be performed with respect to a list of commitments, such as Pedersen commitments sounding in homomorphic cryptographic systems, which may include list of commitments to set of all potential exposed secret test result identifiers across all tests. A prover, such as a user device and/or secure testing apparatus, may demonstrate knowledge of an opening of commitment $C\_i=g9x\ h9z\ h9s'$, for g, h, generators over a group used as a basis for the encryption, by revealing $(z+s)$. Verification may be performed by multiplying each of the commitments by $h9-(z+s)$; for $C\_i$, this will result in a commitment to 1 (i.e., it may be demonstrated that this is an encryption of 1). Thus, knowledge of the opening of an element of the set of commitments may be demonstrated without revealing which element is known or opening the commitment. Furthermore, a one-out-of-many proof may reveal a serial number such that it cannot be issued multiple times for the same element without detection; in the above example, $(z+s)$ may be public and formed using the serial number and secret key of the test kit, and thus duplicate proof attempts may be detected. This may prevent a single result from being reported by many individuals without detection.

As a further non-limiting example, and still referring to FIG. 1, a privacy-preserving function may be performed using a combination of techniques from cryptographic computation families of multiparty computation and oblivious transfer. In one illustrative example, a test issuer may distribute test kits to testers. Each test kit may include code, such as a QR code or other code that is visible, which may have a small number of bits. Each test kit also may include a secret test result, which may have a small number of bits. Test issuer may potentially have recorded which test kit it gave to which tester. In an embodiment, tester may perform test and send to test issuer $g9x\ h9y$ where x and y are random numbers, g and h are group elements over an elliptic curve group such as without limitation Curve25519 and q is a visible code on the test kit. The tester may also use the exposed code from the test kit, here denoted for purposes of discussion as "b," to request a result-specific result from the issuer via oblivious transfer. For instance, for a set of s codes indexed by b, where one of them (s') indicates a positive, an honest positive tester will have revealed the index b that corresponds to s'; to retrieve s', the tester may engage in oblivious transfer with the test issuer, such as without limitation via the chou orlandi scheme. This may prevent test issuer from knowing whether tester has a correct positive b or a different one. As used herein, an "oblivious transfer" is a protocol whereby a recipient, such as without limitation tester, requests one or more values of a plurality of values from a sender, such as without limitation test issuer, which then returns the requested values to recipient, without the sender being able to know which values the sender has transmitted and without the recipient learning any of the plurality of values besides the requested values. Test issuer may determine whether test issuer has previously received a query and/or request for oblivious transfer referencing q; if so, test issuer may ignore request, to avoid attacks where a tester queries repeatedly to undermine the integrity of system 100 by posting multiple results. Issuer may return a numerical code at index b to tester from a list of codes, as part of the oblivious transfer exchange, where numerical code may be implemented in any manner as described above. Note that, by virtue of oblivious transfer protocol, issuer may not know what index tester sent or what code it has sent back to tester. Test issuer may publish $g9x\ h9y\ h9s=g9x\ h9(y+s)$ to data repository 124 or other data store where s is the code that would have been exposed on the test kit if the result were positive. A similar publication, without loss of generality, may be made for negative results. Tester may now create a 1-out-of-many proof as described above to prove a given result without revealing its identity. Value $y+s$, which may be unique and/or unpredictable, may be exposed as part of the proof which may ensure that no party or listener can issue another proof using the same test; in other words, a given test result may be reportable only once if following the protocol. In order to mitigate ability of test issuer or other parties to conduct time correlations between the steps above, the tester may utilize a stochastic delay function, whereby a party receives a message to forward, but selects a random waiting time to forward it, thus eliminating the time correlation between receiving a message and forwarding it. In an embodiment, a stochastic delay, for instance and without limitation drawn from an exponential distribution, may mitigate correlation attacks; stochastic delay function may be employed between each step, possibly with longer waits when there is lower reporting activity on the blockchain. In an embodiment, the above-described protocol may be useful in a situation where secret test result on secure test apparatus 108 is unable to encode sufficient bits to be highly difficult to predict.

With continued reference to FIG. 1, in an embodiment, tester may request a test kit using a native application such as a "mobile app" and/or by way of a web application on a browser or the like. Tester may install a native application either prior to or subsequent to a test. Upon install, tester may send test issuer phone number p, where transmission may be performed using any suitable form of electronic communication including without limitation text messaging such as via simple message service (SMS) or the like. Test issuer may transmit a code $c[p]$ to tester. For each phone code $c[p]$, issuer may have prepared a list of tokens, one per kit. In an embodiment, upon tester installation of a mobile application, request for one or more test kits and/or at least a secure test apparatus 108 and/or other such event, tester may transmit phone code $c[p]$ to test issuer, as well at least an initially visible kit code q as described above that tester has received. Tester may transmit, given group members h, g, and random numbers $v[i]$, $w[i]$, $x[i]$, and $y[i]$, $g9v[i]\ h9w[i]$ and $g9x[i]\ h9y[i]$ for each strip i to issuer and test issuer may transmit in return a number $t[c,i]$ equal to a number of kits in a received package of test kits and/or secure test apparatuses 108 including the code, where g and h are generators of a group as before. For each index value i, tester may publish $g9x[i]\ h9y[i]\ h9s'\{q[i]\}$. Tester may also publish in a separate set $g9v[i]\ h9w[i]\ h9t[c,i]$. Publication may include, without limitation, insertion in data repository 124. Subsequently when tester performs a test, instead of sending $q[i]$ as above, tester may send a 1-out-of-many proof, as above of token where the revealed serial number is $w[i]+t[c,i]$; the use of the serial number may function to prevent multiple requests. It tester may also obtain $s'[q[i]]$ by oblivious transfer on the basis of $q[i]$ and $b\{q[i]\}$. Tester may now be able to produce and send a 1-out-of-many proof of $y[i]+s'\{q[i]\}$, as described above for demonstrating knowledge of an opening of a commitment in a list of commitments, which may be used to prevent double proofs. Above-described procedure may use phone numbers to mitigate timing attack issues while keeping phone numbers unlinkable to test results. No result may be connectable to q and/or phone code.

Still referring to FIG. 1, computing device 104 may be configured to evaluate output of cryptographic function. Evaluation may include verification that cryptographic function is a message of a hash as described above. Where output is a secure proof, computing device 104 may evaluate secure proof this may include receiving a verification datum corresponding to secure proof and evaluating the secure proof as a function of the verification datum. Verification datum, as used herein, is any datum that may be used to aid in evaluation of secure proof. For instance, where secure proof includes a zero-knowledge proof, verification datum may include verification data usable to verify zero-knowledge proof.

With continued reference to FIG. 1, computing device 104 may be configured to transmit, publish and/or store an indication of secret test result 112. Computing device 104 may be configured to store an indication of secret test result 112 and/or output of cryptographic function in a data repository 124. Data repository 124 may include any data structure and/or memory device suitable for storing data, including without limitation a relational database, a key-value retrieval datastore such as a NOSQL database, or any other format or structure for use as a datastore that a person skilled in the art would recognize as suitable upon review of the entirety of this disclosure. Data repository 124 may include any distributed data storage device, including without limitation a distributed hash table or the like. Data repository 124 may include an immutable sequential listing.

Figure 2:
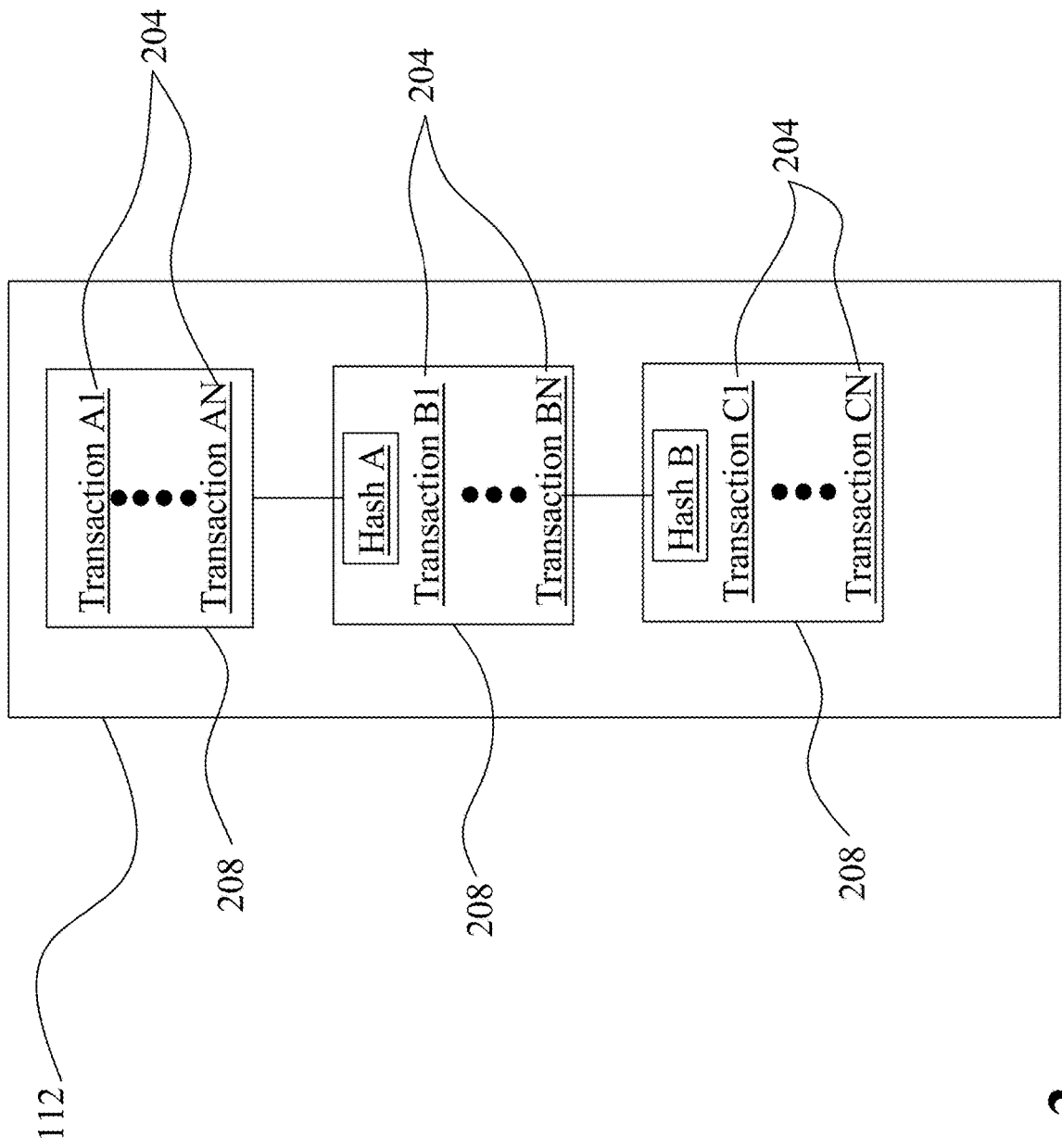
FIG. 2 is a block diagram illustrating an exemplary embodiment of an immutable sequential listing.

Referring now to FIG. 2, an exemplary embodiment of an immutable sequential listing 200 is illustrated. Data elements are listing in immutable sequential listing 200; data elements may include any form of data, including textual data, image data, encrypted data, cryptographically hashed data, and the like. Data elements may include, without limitation, one or more digitally signed assertions. In one embodiment, a digitally signed assertion 204 is a collection of textual data signed using a secure proof as described in further detail below; secure proof may include, without limitation, a digital signature as described above. Collection of textual data may contain any textual data, including without limitation American Standard Code for Information Interchange (ASCII), Unicode, or similar computer-encoded textual data, any alphanumeric data, punctuation, diacritical mark, or any character or other marking used in any writing system to convey information, in any form, including any plaintext or ciphertext data; in an embodiment, collection of textual data may be encrypted, or may be a hash of other data, such as a root 308 or node 304 of a Merkle tree or hash tree, or a hash of any other information desired to be recorded in some fashion using a digitally signed assertion 204. In an embodiment, collection of textual data states that the owner of a certain transferable item represented in a digitally signed assertion 204 register is transferring that item to the owner of an address. A digitally signed assertion 204 may be signed by a digital signature created using the private key associated with the owner's public key, and/or any other suitable digital signature protocol.

Still referring to FIG. 2, a digitally signed assertion 204 may describe a transfer of virtual currency, such as cryptocurrency as described below. The virtual currency may be a digital currency. Item of value may be a transfer of trust, for instance represented by a statement vouching for the identity or trustworthiness of the first entity. Item of value may be an interest in a fungible negotiable financial instrument representing ownership in a public or private corporation, a creditor relationship with a governmental body or a corporation, rights to ownership represented by an option, derivative financial instrument, commodity, debt-backed security such as a bond or debenture or other security as described in further detail below. A resource may be a physical machine e.g. a ride share vehicle or any other asset. A digitally signed assertion 204 may describe the transfer of a physical good; for instance, a digitally signed assertion 204 may describe the sale of a product. In some embodiments, a transfer nominally of one item may be used to represent a transfer of another item; for instance, a transfer of virtual currency may be interpreted as representing a transfer of an access right; conversely, where the item nominally transferred is something other than virtual currency, the transfer itself may still be treated as a transfer of virtual currency, having value that depends on many potential factors including the value of the item nominally transferred and the monetary value attendant to having the output of the transfer moved into a particular user's control. The item of value may be associated with a digitally signed assertion 204 by means of an exterior protocol, such as the COLORED COINS created according to protocols developed by The Colored Coins Foundation, the MASTERCOIN protocol developed by the Mastercoin Foundation, or the ETHEREUM platform offered by the Stiftung Ethereum Foundation of Baar, Switzerland, the Thunder protocol developed by Thunder Consensus, or any other protocol.

Still referring to FIG. 2, in one embodiment, an address is a textual datum identifying the recipient of virtual currency or another item of value in a digitally signed assertion 204. In some embodiments, address is linked to a public key, the corresponding private key of which is owned by the recipient of a digitally signed assertion 204. For instance, address may be the public key. Address may be a representation, such as a hash, of the public key. Address may be linked to the public key in memory of a computing device 104, for instance via a "wallet shortener" protocol. Where address is linked to a public key, a transferee in a digitally signed assertion 204 may record a subsequent a digitally signed assertion 204 transferring some or all of the value transferred in the first a digitally signed assertion 204 to a new address in the same manner. A digitally signed assertion 204 may contain textual information that is not a transfer of some item of value in addition to, or as an alternative to, such a transfer. For instance, as described in further detail below, a digitally signed assertion 204 may indicate a confidence level associated with a distributed storage node 304 as described in further detail below.

In an embodiment, and still referring to FIG. 2 immutable sequential listing 200 records a series of postings in a way that preserves the order in which the postings took place. Temporally sequential listing may be accessible at any of various security settings; for instance, and without limitation, temporally sequential listing may be readable and modifiable publicly, may be publicly readable but writable only by entities and/or devices having access privileges established by password protection, confidence level, or any device authentication procedure or facilities described herein, or may be readable and/or writable only by entities and/or devices having such access privileges. Access privileges may exist in more than one level, including, without limitation, a first access level or community of permitted entities and/or devices having ability to read, and a second access level or community of permitted entities and/or devices having ability to write; first and second community may be overlapping or non-overlapping. In an embodiment, posted content and/or immutable sequential listing 200 may be stored as one or more zero knowledge sets (ZKS), Private Information Retrieval (PIR) structure, or any other structure that allows checking of membership in a set by querying with specific properties. Such database may incorporate protective measures to ensure that malicious actors may not query the database repeatedly in an effort to narrow the members of a set to reveal uniquely identifying information of a given posted content.

Still referring to FIG. 2, immutable sequential listing 200 may preserve the order in which the postings took place by listing them in chronological order; alternatively or additionally, immutable sequential listing 200 may organize digitally signed assertions 204 into sub-listings 208 such as "blocks" in a blockchain, which may be themselves collected in a temporally sequential order; digitally signed assertions 204 within a sub-listing 208 may or may not be temporally sequential. The ledger may preserve the order in which postings took place by listing them in sub-listings 208 and placing the sub-listings 208 in chronological order. The immutable sequential listing 200 may be a distributed, consensus-based ledger, such as those operated according to the protocols promulgated by Ripple Labs, Inc., of San Francisco, Calif., or the Stellar Development Foundation, of San Francisco, Calif., or of Thunder Consensus. In some embodiments, the ledger is a secured ledger; in one embodiment, a secured ledger is a ledger having safeguards against alteration by unauthorized parties. The ledger may be maintained by a proprietor, such as a system administrator on a server, that controls access to the ledger; for instance, the user account controls may allow contributors to the ledger to add postings to the ledger but may not allow any users to alter postings that have been added to the ledger. In some embodiments, ledger is cryptographically secured; in one embodiment, a ledger is cryptographically secured where each link in the chain contains encrypted or hashed information that makes it practically infeasible to alter the ledger without betraying that alteration has taken place, for instance by requiring that an administrator or other party sign new additions to the chain with a digital signature. Immutable sequential listing 200 may be incorporated in, stored in, or incorporate, any suitable data structure, including without limitation any database, datastore, file structure, distributed hash table, directed acyclic graph or the like. In some embodiments, the timestamp of an entry is cryptographically secured and validated via trusted time, either directly on the chain or indirectly by utilizing a separate chain. In one embodiment the validity of timestamp is provided using a time stamping authority as described in the RFC 3161 standard for trusted timestamps, or in the ANSI ASC x9.95 standard. In another embodiment, the trusted time ordering is provided by a group of entities collectively acting as the time stamping authority with a requirement that a threshold number of the group of authorities sign the timestamp.

In some embodiments, and with continued reference to FIG. 2, immutable sequential listing 200, once formed, may be inalterable by any party, no matter what access rights that party possesses. For instance, immutable sequential listing 200 may include a hash chain, in which data is added during a successive hashing process to ensure non-repudiation. Immutable sequential listing 200 may include a blockchain. In one embodiment, a blockchain is immutable sequential listing 200 that records one or more new postings in a data item known as a sub-listing 208 or "block." An example of a blockchain is the BITCOIN blockchain used to record BITCOIN transactions and values. Sub-listings 208 may be created in a way that places the sub-listings 208 in chronological order and link each sub-listing 208 to a previous sub-listing 208 in the chronological order so that any computing device 104 may traverse the sub-listings 208 in reverse chronological order to verify any postings listed in the blockchain. Each new sub-listing 208 may be required to contain a cryptographic hash describing the previous sub-listing 208. In some embodiments, the blockchain contains a single first sub-listing 208 sometimes known as a "genesis block."

Still referring to FIG. 2, the creation of a new sub-listing 208 may be computationally expensive; for instance, the creation of a new sub-listing 208 may be designed by a "proof of work" protocol accepted by all participants in forming the immutable sequential listing 200 to take a powerful set of computing devices 104 a certain period of time to produce. Where one sub-listing 208 takes less time for a given set of computing devices 104 to produce the sub-listing 208 protocol may adjust the algorithm to produce the next sub-listing 208 so that it will require more steps; where one sub-listing 208 takes more time for a given set of computing devices 104 to produce the sub-listing 208 protocol may adjust the algorithm to produce the next sub-listing 208 so that it will require fewer steps. As an example, protocol may require a new sub-listing 208 to contain a cryptographic hash describing its contents; the cryptographic hash may be required to satisfy a mathematical condition, achieved by having the sub-listing 208 contain a number, called a nonce, whose value is determined after the fact by the discovery of the hash that satisfies the mathematical condition. Continuing the example, the protocol may be able to adjust the mathematical condition so that the discovery of the hash describing a sub-listing 208 and satisfying the mathematical condition requires more or less steps, depending on the outcome of the previous hashing attempt. Mathematical condition, as an example, might be that the hash contains a certain number of leading zeros and a hashing algorithm that requires more steps to find a hash containing a greater number of leading zeros, and fewer steps to find a hash containing a lesser number of leading zeros. In some embodiments, production of a new sub-listing 208 according to the protocol is known as "mining." The creation of a new sub-listing 208 may be designed by a "proof of stake" protocol as will be apparent to those skilled in the art upon reviewing the entirety of this disclosure.

Continuing to refer to FIG. 2, in some embodiments, protocol also creates an incentive to mine new sub-listings 208. The incentive may be financial; for instance, successfully mining a new sub-listing 208 may result in the person or entity that mines the sub-listing 208 receiving a predetermined amount of currency. The currency may be fiat currency. Currency may be cryptocurrency as defined below. In other embodiments, incentive may be redeemed for particular products or services; the incentive may be a gift certificate with a particular business, for instance. In some embodiments, incentive is sufficiently attractive to cause participants to compete for the incentive by trying to race each other to the creation of sub-listings 208. Each sub-listing 208 created in immutable sequential listing 200 may contain a record or posting describing one or more addresses that receive an incentive, such as virtual currency, as the result of successfully mining the sub-listing 208.

With continued reference to FIG. 2, where two entities simultaneously create new sub-listings 208, immutable sequential listing 200 may develop a fork; protocol may determine which of the two alternate branches in the fork is the valid new portion of the immutable sequential listing 200 by evaluating, after a certain amount of time has passed, which branch is longer. "Length" may be measured according to the number of sub-listings 208 in the branch. Length may be measured according to the total computational cost of producing the branch. Protocol may treat only postings contained in the valid branch as valid postings. When a branch is found invalid according to this protocol, postings registered in that branch may be recreated in a new sub-listing 208 in the valid branch; the protocol may reject "double spending" postings that transfer the same virtual currency that another posting in the valid branch has already transferred. As a result, in some embodiments the creation of fraudulent postings requires the creation of a longer immutable sequential listing 200 branch by the entity attempting the fraudulent postings than the branch being produced by the rest of the participants; as long as the entity creating the fraudulent postings is likely the only one with the incentive to create the branch containing the fraudulent postings, the computational cost of the creation of that branch may be practically infeasible, guaranteeing the validity of all postings in the immutable sequential listing 200.

Still referring to FIG. 2, additional data linked to postings may be incorporated in sub-listings 208 in the immutable sequential listing 200; for instance, data may be incorporated in one or more fields recognized by blockchain protocols that permit a person or computer forming a posting to insert additional data in the immutable sequential listing 200. In some embodiments, additional data is incorporated in an unspendable postings field. For instance, the data may be incorporated in an OP_RETURN within the BITCOIN blockchain. In other embodiments, additional data is incorporated in one signature of a multi-signature posting. In an embodiment, a multi-signature posting is posting to two or more addresses. In some embodiments, the two or more addresses are hashed together to form a single address, which is signed in the digital signature of the posting. In other embodiments, the two or more addresses are concatenated. In some embodiments, two or more addresses may be combined by a more complicated process, such as the creation of a Merkle tree or the like. In some embodiments, one or more addresses incorporated in the multi-signature posting are typical cryptocurrency addresses, such as addresses linked to public keys as described above, while one or more additional addresses in the multi-signature posting contain additional data related to the posting; for instance, the additional data may indicate the purpose of the posting, aside from an exchange of virtual currency, such as the item for which the virtual currency was exchanged. In some embodiments, additional information may include network statistics for a given node 304 of network, such as a distributed storage node 304, e.g. the latencies to nearest neighbors in a network graph, the identities or identifying information of neighboring nodes 304 in the network graph, the trust level and/or mechanisms of trust (e.g. certificates of physical encryption keys, certificates of software encryption keys, (in non-limiting example certificates of software encryption may indicate the firmware version, manufacturer, hardware version and the like), certificates from a trusted third party, certificates from a decentralized anonymous authentication procedure, and other information quantifying the trusted status of the distributed storage node 304) of neighboring nodes 304 in the network graph, IP addresses, GPS coordinates, and other information informing location of the node 304 and/or neighboring nodes 304, geographically and/or within the network graph. In some embodiments, additional information may include history and/or statistics of neighboring nodes 304 with which the node 304 has interacted. In some embodiments, this additional information may be encoded directly, via a hash, hash tree or other encoding.

With continued reference to FIG. 2, in some embodiments, virtual currency is traded as a cryptocurrency. In one embodiment, a cryptocurrency is a digital currency such as Bitcoins, Peercoins, Namecoins, and Litecoins. Cryptocurrency may be a clone of another cryptocurrency. The cryptocurrency may be an "alt-coin." Cryptocurrency may be decentralized, with no particular entity controlling it; the integrity of the cryptocurrency may be maintained by adherence by its participants to established protocols for exchange and for production of new currency, which may be enforced by software implementing the cryptocurrency. Cryptocurrency may be centralized, with its protocols enforced or hosted by a particular entity. For instance, cryptocurrency may be maintained in a centralized ledger, as in the case of the XRP currency of Ripple Labs, Inc., of San Francisco, Calif. In lieu of a centrally controlling authority, such as a national bank, to manage currency values, the number of units of a particular cryptocurrency may be limited; the rate at which units of cryptocurrency enter the market may be managed by a mutually agreed-upon process, such as creating new units of currency when mathematical puzzles are solved, the degree of difficulty of the puzzles being adjustable to control the rate at which new units enter the market. Mathematical puzzles may be the same as the algorithms used to make productions of sub-listings 208 in a blockchain computationally challenging; the incentive for producing sub-listings 208 may include the grant of new cryptocurrency to the miners. Quantities of cryptocurrency may be exchanged using one or more postings as described above.

Referring again to FIG. 1, computing device 104 may be configured to generate secret test result and/or to receive secret test result 112 from another device (not shown). Computing device 104 may be configured to generate a commitment to secret test result 112; cryptographic function as described above may output a secure proof that is a proof of the commitment. Commitment may include any cryptographic commitment, defined as a process whereby a device and/or entity selects an element from a set of possible elements, such as a keyspace or the like, in such a way that another entity finds it at least computationally infeasible to identify the element, but for which a process, known as "opening" the commitment, may be used to prove that the commitment is to that element. Commitment may include any suitable process therefor, including without limitation a Pedersen commitment. Alternatively or additionally, commitment may be performed by inclusion of secret test result 112 in a cryptographic accumulator.

Figure 3:
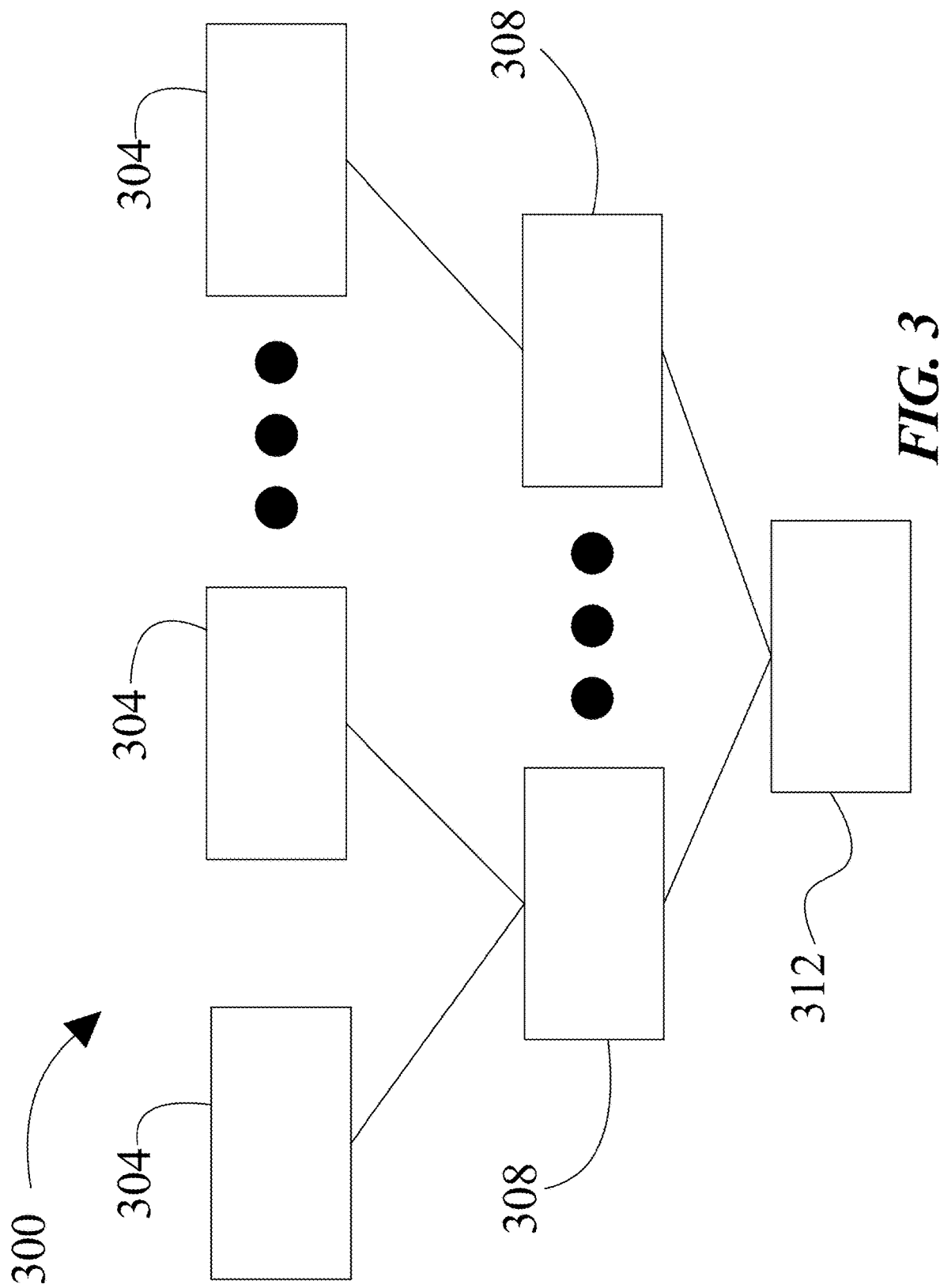
FIG. 3 is a block diagram illustrating an exemplary embodiment of a cryptographic accumulator.

Referring to FIG. 3, an exemplary embodiment of a cryptographic accumulator 300 is illustrated. A "cryptographic accumulator," as used in this disclosure, is a data structure created by relating a commitment, which may be smaller amount of data that may be referred to as an "accumulator" and/or "root 312," to a set of elements, such as lots of data and/or collection of data, together with short membership and/or nonmembership proofs for any element in the set. In an embodiment, these proofs may be publicly verifiable against the commitment. An accumulator may be said to be "dynamic" if the commitment and membership proofs can be updated efficiently as elements are added or removed from the set, at unit cost independent of the number of accumulated elements; an accumulator for which this is not the case may be referred to as "static." A membership proof may be referred to as a as a "witness" whereby an element existing in the larger amount of data can be shown to be included in the root 312, while an element not existing in the larger amount of data can be shown not to be included in the root 312, where "inclusion" indicates that the included element was a part of the process of generating the root 312, and therefore was included in the original larger data set.

Turning now to FIG. 3, an exemplary embodiment of a cryptographic accumulator is illustrated. Cryptographic accumulator has a plurality of accumulated elements 304, each accumulated element 304 generated from a lot of the plurality of data lots. Accumulated elements 304 are create using an encryption process, defined for this purpose as a process that renders the lots of data unintelligible from the accumulated elements 304; this may be a one-way process such as a cryptographic hashing process and/or a reversible process such as encryption. Cryptographic accumulator further includes structures and/or processes for conversion of accumulated elements 304 to root 312 element. For instance, and as illustrated for exemplary purposes in FIG. 3, cryptographic accumulator may be implemented as a Merkle tree and/or hash tree, in which each accumulated element 304 created by cryptographically hashing a lot of data. Two or more accumulated elements 304 may be hashed together in a further cryptographic hashing process to produce a node 308 element; a plurality of node 308 elements may be hashed together to form parent nodes 308, and ultimately a set of nodes 308 may be combined and cryptographically hashed to form root 312. Contents of root 312 may thus be determined by contents of nodes 308 used to generate root 312, and consequently by contents of accumulated elements 304, which are determined by contents of lots used to generate accumulated elements 304. As a result of collision resistance and avalanche effects of hashing algorithms, any change in any lot, accumulated element 304, and/or node 308 is virtually certain to cause a change in root 312; thus, it may be computationally infeasible to modify any element of Merkle and/or hash tree without the modification being detectable as generating a different root 312. In an embodiment, any accumulated element 304 and/or all intervening nodes 308 between accumulated element 304 and root 312 may be made available without revealing anything about a lot of data used to generate accumulated element 304; lot of data may be kept secret and/or demonstrated with a secure proof as described below, preventing any unauthorized party from acquiring data in lot.

Alternatively or additionally, and still referring to FIG. 3, cryptographic accumulator may include a "vector commitment" which may act as an accumulator in which an order of elements in set is preserved in its root 312 and/or commitment. In an embodiment, a vector commitment may be a position binding commitment and can be opened at any position to a unique value with a short proof (sublinear in the length of the vector). A Merkle tree may be seen as a vector commitment with logarithmic size openings. Subvector commitments may include vector commitments where a subset of the vector positions can be opened in a single short proof (sublinear in the size of the subset). Persons skilled in the art, upon reviewing the entirety of this disclosure, will be aware of various alternative or additional cryptographic accumulators that may be used as described herein. In addition to Merkle trees, accumulators may include without limitation RSA accumulators, class group accumulators, and/or bi-linear pairing-based accumulators. Any accumulator may operate using one-way functions that are easy to verify but infeasible to reverse, i.e. given an input it is easy to produce an output of the one-way function but given an output it is computationally infeasible and/or impossible to generate the input that produces the output via the one-way function. For instance, and by way of illustration, a Merkle tree may be based on a hash function as described above. Data elements may be hashed and grouped together. Then, the hashes of those groups may be hashed again and grouped together with the hashes of other groups; this hashing and grouping may continue until only a single hash remains. As a further non-limiting example, RSA and class group accumulators may be based on the fact that it is infeasible to compute an arbitrary root of an element in a cyclic group of unknown order, whereas arbitrary powers of elements are easy to compute. A data element may be added to the accumulator by hashing the data element successively until the hash is a prime number and then taking the accumulator to the power of that prime number. The witness may be the accumulator prior to exponentiation. Bi-linear paring-based accumulators may be based on the infeasibility found in elliptic curve cryptography, namely that finding a number k such that adding P to itself k times results in Q is impractical, whereas confirming that, given 4 points P, Q, R, S, the point, P needs to be added as many times to itself to result in Q as R needs to be added as many times to itself to result in S, can be computed efficiently for certain elliptic curves.

In an embodiment, and still referring to FIG. 3, where secret test result identifier is encoded with an error correction code, an output may be generated as a function of an error correction function as described above. In an embodiment, error correction function may be performed by computing device 104; for instance, computing device may perform error correction on output before or after generation of cryptographic function. In an embodiment, and without limitation, cryptographic output may be transmitted in two or more redundant portions and a Hamming distance between portions may be used to correct erroneous bits. Redundant portions may be generated based on redundant portions of secret 112, such that Hamming distances between portions of secret 112 correspond to Hamming distances between outputs, permitting error correction and/or detection. Alternatively or additionally, secure test apparatus and/or another apparatus such as a user device or the like may perform error correction prior to and/or simultaneously with error correction function.

In operation, a test and/or plurality of secure testing apparatuses may be distributed to a population of individuals, possibly determined by geography or other characteristics. Each individual issued a test may perform a test, for instance using secure testing apparatus, and report a result as described above. An issuing party of test and/or other observers may then reach conclusions about prevalence of various conditions based upon the reported test result.

Such processes may alternatively or additionally be used for contact tracing. If individuals report positive test results, then this may be used to enable a system where others who had recently been in contact with a positive individual can determine that they may have been exposed to a positive individual. For example, a smart phone-app may exchange random ID numbers with all nearby phones, that each record the IDs. Later, if someone has a positive test result and reports this along with the ID numbers issued or received, or some cryptographic function thereof, then this data may be used for anyone to determine whether they had been near a positive person without revealing the identity of any individuals involved and without the involvement of any trusted party at any point following preparation of the tests (and in particular without involvement of any trusted party in the performance of tests). The data store may be a blockchain or a trusted database. Note that if a test is one that is positive indefinitely following any exposure, rather than only during active infection, then a protocol may be used as follows. If a person has periodically been reporting negative serological tests and now reports a positive one, this may indicate active infection. An app and/or other element as described above may provide a proof of the prior negatives and the new positive, and this may be used for anonymous contact tracing as anyone who went near that phone (as known by reports to the data store of random IDs) may now know that they had been near someone that has tested positive (without knowing the identity of that person).

In an embodiment, and without limitation, system 100 may perform one or more privacy-preserving contact-tracing processes. For instance, and without limitation where users of system 100 use client devices such as smartphones, tablets, and/or any device suitable for use as a secure test apparatus as described above, each such device may share cryptographic information with neighbors that allows local graph computations. In contrast to a contact tracing methods that rely on phones coming in close proximity and connecting with each other by local wireless protocols, devices, and/or components, such as the BLUETOOTH protocol promulgated by Bluetooth SIG, Inc. of Kirkland, Washington or the like, system 100 may be configured to alert not only people whose client devices directly communicated with a client device of a user who tested positive for a given infectious disease, but also individuals whose client devices did not interact with the client device of the positive user. In an embodiment, a decentralized system may be able to determine that a user device is two degrees away from an infected person via multiple paths, or other such graph metrics, without anyone having access to a full contact graph, and without revealing to any person an identity of an infected individual.

In an embodiment, system 100 and/or computing device 104 may receive, from each user device, at least a contact communication. Each user may be able to specify a level of time, location, and degree-of-separation detail to be transmitted. System 100 and/or computing device 104 may use inputs from a plurality of user devices and/or secure testing apparatuses 112 to generate a graph indicating a history of contacts between user devices; graph may include any suitable data structure for representation of a graph, including a plurality of nodes having links and/or pointers to other nodes. Each node may represent, without limitation, a user device and/or secure testing apparatus 112. Nodes may have edge and/or link data elements indicating contacts with devices, or users thereof, represented by other nodes, where a contact between a first device and a second device may be recorded, without limitation, by a data element stored in the first node indicating the second node and a data element stored in the second node indicating the second node. A "contact," as used in this disclosure, is an event in which a first user device comes into close proximity to a second device; close proximity may indicate approach within a threshold distance of the second device. Close proximity may further include location within a threshold distance for a threshold quantity of time. In some embodiments, a contact may include a combination of proximity and time considered sufficient for transmission of a contagious pathogen such as COVID 19 or the like.

In an embodiment, a first secure test apparatus 112 and/or user device may be determined to be at a location where a test was performed and/or a location at which a second user device and/or secure test apparatus 112, such as one operated by a user having a positive test, was located at the same time as the first device. In an embodiment, this determination may be performed by means of a trust network-based probabilistic location proof and/or other process that can determine where a device associated with a node is likely to have been at any given point in time.

In an embodiment, and still referring to FIG. 1, system 100, computing device 104, and/or any other device in communication with system 100 may perform and/or evaluate probabilistic location evaluations and/or proofs. In an embodiment, devices represented by nodes and/or devices in a network may include any device transmitting and/or receiving data, including without limitation user devices, secure test apparatuses 112, cell towers, GPS satellites, cameras or the like. Each or any such device may have a private key. Private key may include, without limitation, any private key and/or other secret information suitable for use in generating a digital signature as described above. An application operating on any device may determine that the device is located near to an apparatus associated with a given node by contacting nearby apparatuses and transmitting to the nearby apparatuses a request for a digital signature on a message stating information that is informative about a distance from the device to that apparatus. For example, a message may indicate that the device utilized a local mode of communication, such as communication via BLUETOOTH protocol, to communicate with apparatus, which may indicate that device may be within range of the local mode of communication; alternatively or additionally, message may include a timestamp generated at transmission from device to apparatus and/or at time of signing by apparatus, which may indicate network loop and/or round trip latency time, from which distance may be determined and/or estimated. Message may alternatively or additionally include any data from location detection devices and/or systems, which may include one or more satellite-based navigation facilities such as the Global Positioning System (GPS), GLONASS, Galileo, BeiDou, QZSS, IRNSS and/or NavIC. Device may receive a plurality of such messages from apparatuses and/or nodes. In an embodiment, application operating on device may provide signed message or messages to any verifier, which may include any device in and/or communicating with system 100 along with a purported latitude and longitude of device, for instance as generated by device using any geographical location process as above; verifier, such as for instance computing device 104, may compute a statistical calculation, such as a Bayesian calculation, of a level of confidence in the purported location based on a level of trust in how supportive each signed message is of the given location.

With further reference to FIG. 1, a Bayesian calculation and/or other probabilistic calculation may be used to estimate and/or predict a location of a device such as a secure test apparatus 112 and/or user device. In an embodiment, an initial and/or prior estimate for a location of a device may be calculated; initial and/or prior estimate may be based on one or more previous iterations of method described in this disclosure, including without limitation a previous iteration of a probabilistic calculation as described herein. Alternatively or additionally, initial and/or prior estimate may be determined using IP geolocation, a location of one or more devices in communication with device, or the like. A device performing probabilistic calculation may construct a likelihood, P(data_from_devices|location) representing a conditional probability of certain data given a particular location. Likelihood may in turn be used to computing a posterior, P(location|data_from_devices), which may represent a probability of a particular location given data_from_devices, where "data_from_devices" represents data received from other devices concerning device as described above. This value may be calculated using an application of Bayes' Theorem or Bayes' Rule:

$$P(A \mid B) = \frac{P(B \mid A)P(A)}{P(B)}$$

where P(A|B) represents a likelihood of A given B being true, P(B|A) represents a likelihood of B given A being true, and P(A) and P(B) represent probabilities of A and B, respectively. For instance and without limitation, probability of a location being accurate give data from devices may be represented in the following equation:

$$P(\text{location} \mid \text{data\_from\_devices}) = \frac{P(\text{data\_from\_devices} \mid \text{location}) P(\text{location})}{P(\text{data\_from\_devices})}$$

which may reflect a "belief," degree of confidence, and/or probabilistic estimate about location after having combined data_from_devices with initial and/or prior estimate. In an embodiment, this may generate a "bootstrapped" trust network, wherein a degree of confidence in data reported by other devices P(data_from_devices), a degree of confidence in such data given a putative location of device P(data_from_devices|location), and an initial degree of confidence in putative location P(location) may be used to determine a degree of confidence in location based on the data reported by the other devices. A degree of confidence in data_from_devices, which may include data such as whether the additional devices could communicate with device over bluetooth, ping times, and/or other information as described above, may each have been computed in the same way, as described above, including without limitation using Bayes' Rule, based on how much trust a user administering system 100 has placed in the devices a priori, and/or by one or more alternative or additional methods of assigning trust to devices. Assignment of trust to devices may be performed, without limitation, using a known association of such devices with institutions and/or networks having some known and/or stored degree of reliability; for instance, and without limitation, a device that is a part of a regularly used and/or regulated communication infrastructure may be assigned a higher confidence level than a device that is not so deployed, while the latter device may require use of probabilistic calculations as described above by reference to data exchanged with other devices or the like. This may be performed recursively, calculating a series of confidence levels in data from devices based on previously calculated confidence levels in such data from other devices, which may emanate from one or more initial assigned values relating to devices having high degrees of confidence as described above.

Still referring to FIG. 1, each apparatus and/or device represented by a node may establish and/or prove a location of such apparatus and/or device, for instance and without limitation by performing any step described above.

With continued reference to FIG. 1, locations of a plurality of devices may be combined with timestamps to determine that two given devices have been in close proximity as described above at any given time and may further be used to determine a duration of such proximity; this may be used to perform contact tracing. In addition, given an ability to provide a decentralized argument for location at a given time, a device and/or operation in system 100 may be able to provide an argument for speed by providing two arguments for location of a single device with the time for each, taking the distance between the two locations, and dividing by the time elapsed; this may allow analyzers to compute whether an infected person was moving quickly or slowly at a given time in order to inform model construction for infection spread.

If a trusted party signs on a test result, such as with a digital signature, and reports this to a public data store, then a tested party may later prove the result without revealing its identity or revealing any information that had been exposed to even the trusted party; for example, the tested party can produce a one-out-of-many cryptographic proof that it knows one of the values in the set of all values corresponding to all positive (or negative) results certified by the trusted party, without revealing that value.

Figure 4:
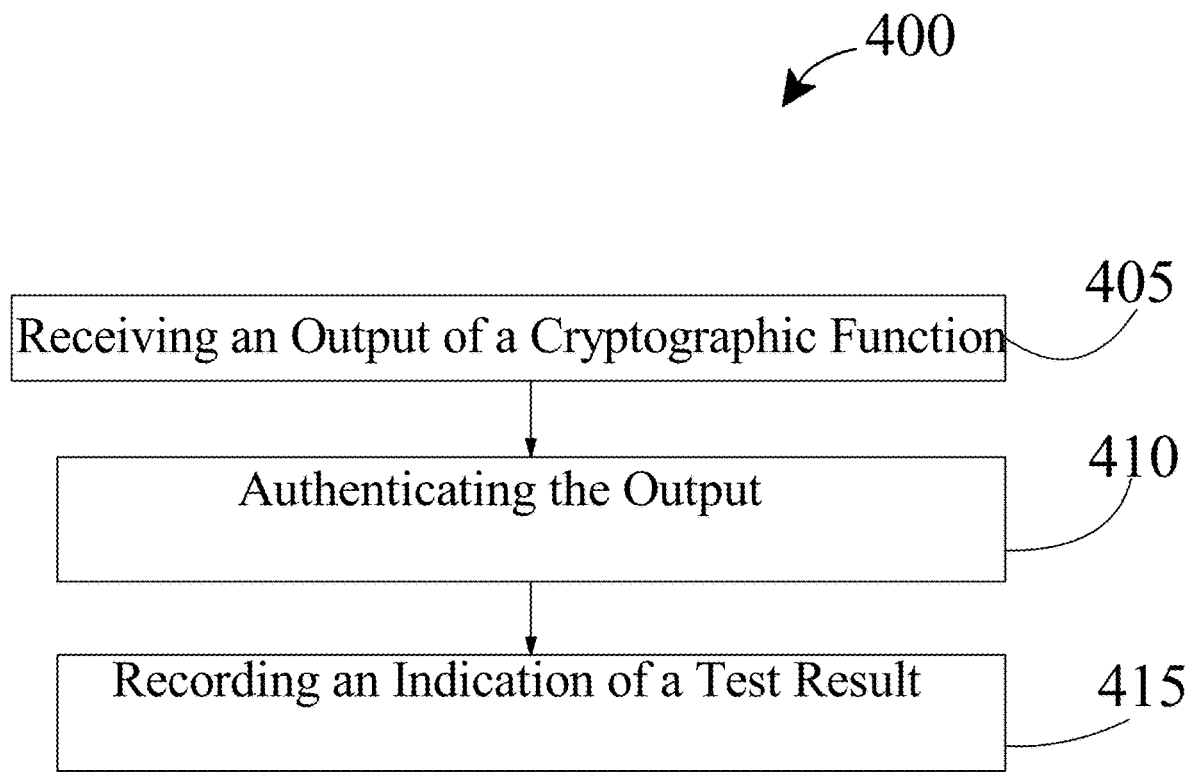
FIG. 4 is a flow diagram illustrating an exemplary embodiment of a method of cryptographically secured decentralized testing.

Referring now to FIG. 4, an exemplary embodiment of a method 400 of cryptographically secured decentralized testing is illustrated. At step 405, a computing device 104 receives from a secure test apparatus 108, an output of a cryptographic function of a secret test result identifier; this may be accomplished, without limitation, as described above in reference to FIGS. 1-3. Output may include a cryptographic hash of the secret test result identifier. Output may include a secure proof of the secret test result identifier. Computing device 104 may generate a commitment to the secret test result 112, and secure proof may include a proof of the commitment. Commitment may include a cryptographic accumulator, and proof of the commitment may include a proof of membership in the cryptographic accumulator. At step 410, computing device 104 authenticates output; this may be accomplished, without limitation, as described above in reference to FIGS. 1-3.

At step 415, and still referring to FIG. 4, computing device 104 records an indication of the output in a data repository 124; this may be accomplished, without limitation, as described above in reference to FIGS. 1-3. Data repository 124 may include an immutable sequential listing.

Figure 5:
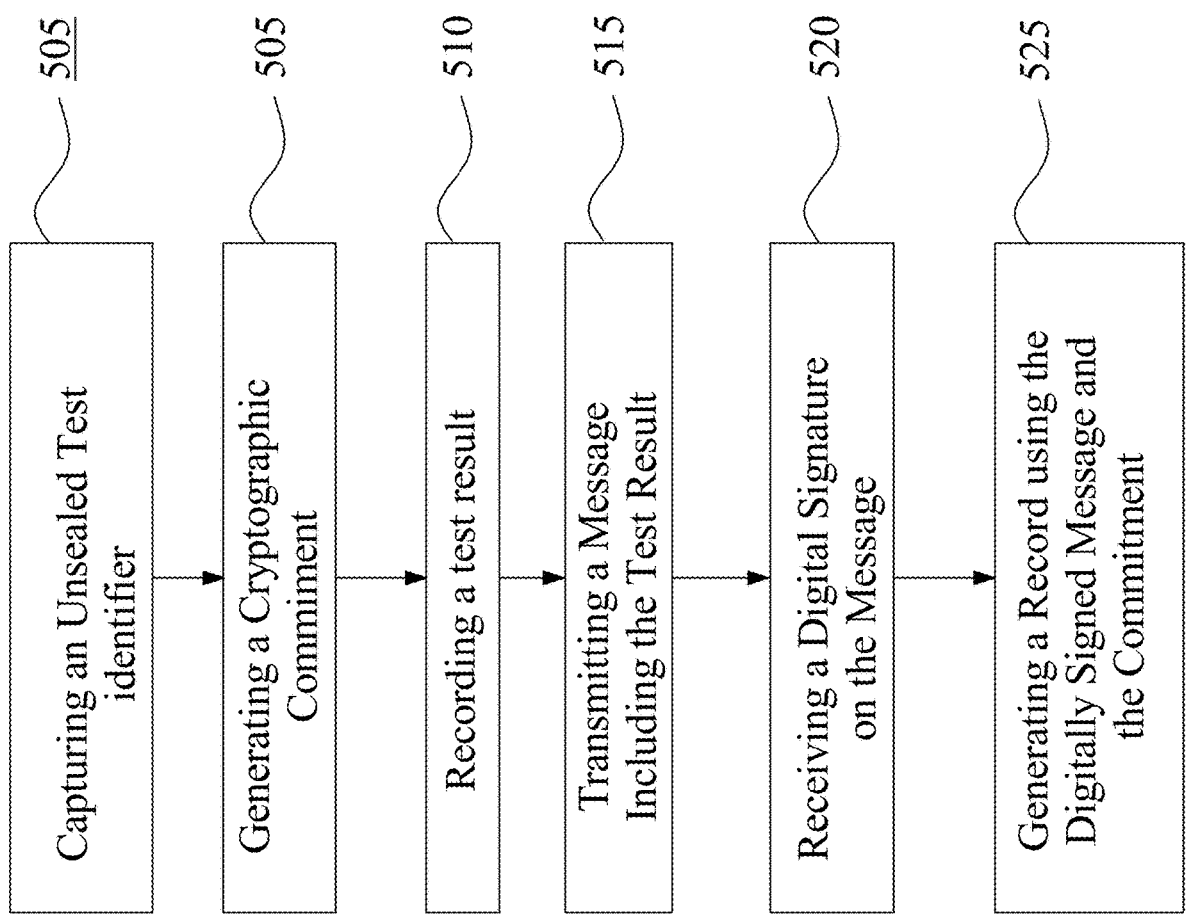
FIG. 5 is a flow diagram illustrating an exemplary embodiment of a method of cryptographically secured decentralized testing.

Referring now to FIG. 5, an exemplary embodiment of a method 500 of cryptographically secured medical testing is illustrated. Method 500 may be performed by a computing device and/or set thereof as configured using instructions in a non-transitory memory, where a "non-transitory" memory is any memory that continues to store instructions if not actively powered by a power source. Non-transitory memory may include without limitation any component and/or technology suitable for use as a secondary memory as described in further detail below. At step 505, a computing device captures an unsealed test identifier corresponding to a test apparatus. An unsealed test identifier is a test identifier that is only accessible to a computing device, secure test apparatus, or the like, when a test is opened for administration, for instance by unsealing a packet containing the test or the like; this may be implemented, without limitation, in any manner described above in reference to FIGS. 1-4. Test apparatus may include any suitable test apparatus as described in this disclosure, including without limitation a secure test apparatus. In some embodiments, test apparatus may have a degradation period associated therewith; that is, test apparatus may become inoperable and/or unreliable after a period of time, which may be denoted for the purposes of this disclosure as a "degradation period." For instance, a test kit or strip included in and/or part of test composed such that it quickly degrades when exposed to air and/or light. In an exemplary embodiment, the test may include indicator film with colorimetric assays, such as those used for pH testing, chlorine content testing, and the like. For example, one exemplary colorimetric assay may be β-cyclodextrin grafted chitosan/montmorillonite with methylene blue/glucose system. A test may be distributed in a sealed package such that when someone opens it, they must be ready to perform the test within the degradation period.

At step 510, and still referring to FIG. 5, computing device generates a cryptographic commitment to the unsealed test identifier; cryptographic commitment may include, without limitation, any cryptographic commitment as described in this disclosure. Generating cryptographic commitment may include posting the cryptographic commitment to an immutable sequential listing; this may be accomplished in any manner described above in reference to FIGS. 1-4. In some embodiments, posting to an immutable sequential listing may provide evidence of a time at which sealed identifier was captured and/or test was performed; for instance, posting of a commitment in a sublisting or block i of an immutable sequential listing may serve as evidence that a test was performed after the time that block i was started.

At step 515, and continuing to refer to FIG. 5, computing device records a test result from the test apparatus; this may be accomplished in any manner described above in reference to FIGS. 1-4.

At step 520, and still referring to FIG. 5, computing devices transmits a message including the test result to at least a local device. At least a local device may include at least a computing device, which may include any computing device as described in this disclosure. At least a local device may include a plurality of local devices, which may be owned and/or operated independently of one another. At least a local device may include a plurality of local devices. Message may include a location of the computing device. Message may include a timestamp. Message may include a value from a most recent state of an immutable sequential listing, where value may include without limitation a cryptographic hash of a current state, of one or more postings, of a current block and/or sublisting, or the like. Message and/or any component thereof may be cryptographically hashed or otherwise altered and/or compressed in a manner that is reproducible to permit identification of the message and/or portion thereof, so altered. Each local device may sign on the message, which may include any combination of test result, an aforementioned cryptographic commitment, a value from the most recent blockchain state (say from block j), and/or a location of computing device and/or local device, for instance and without limitation by "signing on location" according to location determination methods described above.

At step 525, and further referring to FIG. 5, computing device receives a digital signature on the message from the at least a local device; digital signature may be implemented in any manner as described above in reference to FIGS. 1-4.

At step 530, and still referring to FIG. 5, computing device generates a record, the record including digitally signed message and a secure proof of the commitment; secure proof may include any secure proof as described above in reference to FIGS. 1-4. For instance, and without limitation, secure proof may include a zero-knowledge proof. Secure proof may include a one-out-of-many proof; this may be implemented in any manner described in this disclosure.

Computing device may post record to an immutable sequential listing; this may be implemented in any manner described above in reference to FIGS. 1-4. For instance, in some embodiments, commitment may include a cryptographic accumulator, and a proof of the commitment may include a proof of membership in the cryptographic accumulator, for instance and without limitation as described above in reference to FIGS. 1-4. A signed result package, or in other words, the signed message, may then be reported to be recorded on an immutable sequential listing such as a blockchain. In some embodiments, based on the two blockchain commitments such as a first posting in a first block and/or sublisting and result package and/or record in a second block and/or sublisting, it may be possible to show that a test was performed between a conclusion time of the first block and/or sublisting and the conclusion time of a second block and/or sublisting, and that the test was (probabilistically) in a given location at a giving time. To be considered valid, a time elapsed between the conclusion of postings may be required should be less than a degradation period as described above. In some embodiments, given an ability to perform decentralized verifiable testing with probabilistic evidence for time and location of each test, one or more applications may be possible. For instance, a combination of testing and location reporting as described above may be applied to for the purpose of decentralized mapping over time and space. Methods and apparatuses as described above may permit anyone to perform a verifiable test and report a result thereof with location and timing evidence; this data may be integrated over reports to obtain a probabilistic geospatial map over time. Standard statistical techniques may be applied to calculate confidence intervals. Some exemplary standard statistical techniques that may be applied may include using the standard deviation, Fisher's Information metric, and the like.

With further reference to FIG. 5, although examples described above have pertained to a test result and/or identifier captured from a test apparatus, any step or sequence of steps described above may alternatively or additionally be used to record and/or verify one or more sensor readings, which may be captured instead of test results; any secret information, code, cryptographic key, or the like may be substituted for unsealed test identifier. As a result, any sensor reading or set of sensor readings may be recorded, for instance on an immutable sequence listing, using a first posting having a commitment to a secret and a second posting including one or more digital signatures of local devices. Such posting pairs may be evaluated singly or in aggregation to determine sensor readings and/or patterns thereof over regions and/or over time, for instance and without limitation as described in further detail below.

Figure 6:
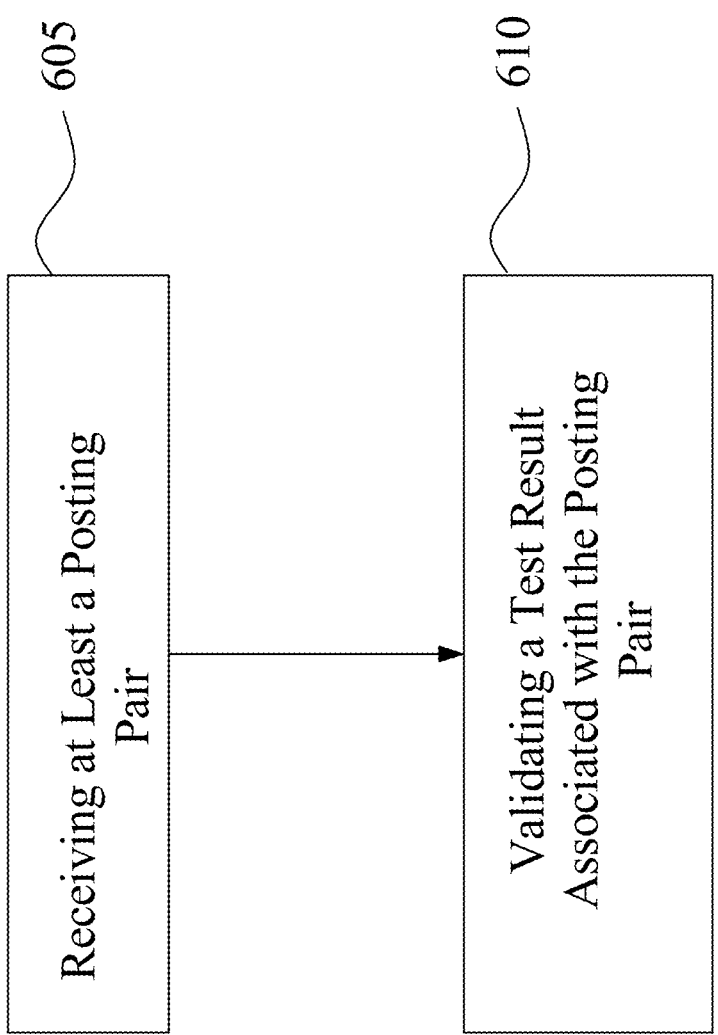
FIG. 6 is a flow diagram illustrating an exemplary embodiment of a method of cryptographically secured decentralized testing.

Referring now to FIG. 6, an exemplary embodiment of a method 600 of cryptographically secured medical testing is illustrated. Method 600 may be performed by a computing device and/or set thereof as configured using instructions in a non-transitory memory. At step 605, a computing device receives at least a posting pair. Receiving each posting pair of at least a posting pair includes locating, at an immutable sequential listing, a first entry including a commitment to an unsealed test identifier and/or other secret as described above; first posting may be implemented as described above in reference to FIG. 5. Receiving each posting pair of at least a posting pair includes locating, at immutable sequential listing, a second entry including a record, the record including a digitally signed message containing a test result and/or sensor readout as described above corresponding to the unsealed test identifier, and a secure proof of the commitment; second posting may be implemented without limitation as described above in reference to FIG. 5. Given a decentralized network for testing with verifiable time and location information, the data reported may be utilized for various mapping and predictive artificial intelligence purposes.

At step 610, and still referring to FIG. 6, computing device validates the test result and/or sensor readout associated with each posting pair of the at least a posting pair. Validation, as used herein, may include a process whereby a test result and/or other sensor readout is determined to be valid and usable. Validating test result verifying secure proof of posting pair, verifying signature of the posting pair, and validating the test result associated with the posting pair as a function of the secure proof and the signature. In some embodiments, validating test result may include determining a time period between the first posting and the second posting, and validating the test result as a function of the time period. For instance, a difference in time between a time in which a sublisting and/or state containing first posting was created and a time in which a sublisting and/or state containing second posting was created may be measured, and/or between a timestamp in and/or associated with first posting and a timestamp in and/or associated with second posting. In some embodiments, where test result is associated with a degradation period, validating the test result as a function of a time period may include comparing the time period to the degradation period and validating the test result as a function of the comparison. For instance, where a time between first posting and second posting is within degradation period, a test result and/or sensor readout may be valid, whereas if such time is greater than degradation period, test result and/or sensor readout may be treated as invalid.

In some embodiments, and further referring to FIG. 6, validating test may include determining a location associated with the test result and validating the test result as a function of the location. For instance, and without limitation, a location reported by a computing device creating first posting may be compared to a location of a local device, and/or locations of a plurality of local devices, to determine if such locations are close enough to one another to be considered likely to be the result of a validly recorded test result and/or sensor reading; local device locations may similarly be compared to one another. In some embodiments, location may be associated with a confidence value; for instance, a probability that a location of test is at a particular point may be determined using reported and/or signed locations of one or more local devices. For example, the confidence value associated with a location may be calculated using a Bayesian calculation as described above with reference to FIG. 1. However, other probabilistic calculation may also be used to determine a confidence level associated with a location. Validating test result as a function of location may include validating the test result as a function of the confidence value; for instance, where location of device performing first posting is not determinable above a given preconfigured threshold probability, test result may be treated as unreliable. In one embodiment, the performer may optionally include with both the checkin blockchain publication and results blockchain publication a cryptographic commitment to the identity of certain blockchain funds and a proof of possessing the knowledge required to spend those funds. This mitigates the risk of collusion between two conspirators located in different locations, where a party opens and performs the test and communicates with another party located in a different location, with that second party reporting the result from its location. If the blockchain messages involve showing knowledge required to spend funds, then such collusion between the parties would entail both parties being able to spend the funds in question. Alternatively, test result and/or sensor reading may be treated as reliable, but location specifically may be ignored and/or not relied upon for determinations as described in further detail below.

In some embodiments, and with continued reference to FIG. 6, computing device may make one or more determinations based on multiple posting pairs. As an example, a reliable map of viral spread may be generated through means of decentralized testing with location and time demonstration. This technique may alternatively or additionally be used for any other verifiable decentralized privacy-preserving tests, such as air quality testing, water quality testing, or the like. For instance, and without limitation, at least a posting pair may include a plurality of posting pairs, and computing device may generate a current prevalence map, where a "current prevalence map" indicates a likely current prevalence of a pathogen or the like over a given region as a function of the plurality of posting pairs; current prevalence map may include a graphical representation of current locations at which positive and/or negative results for a given pathogen have been detected, and/or a forecasted and/or probabilistically calculated density of cases or the like as determined by current locations, which probabilistic calculation may be performed, without limitation, using machine learning or other models as described in further detail below.

Still referring to FIG. 6, computing device may generate a past spread map as a function of a plurality of posting pairs. A past spread map may include a map indicating a progression of spread over a region of a pathogen or other sensed phenomenon; this may be calculated using a series of prevalence maps determined using a series posting pairs captured at some intervals in locations within a mapped region. Alternatively or additionally, probable past prevalence and/or spread thereof may be determined by matching a function representing rates of spread over space and time to points and times of detection and/or a time series of previously and currently determined spread maps; such function may be used to estimate a past prevalence map at an earlier time. Such matching and/or function may be determined using machine-learning as described in this disclosure.

Further referring to FIG. 6, computing device may generate a projected future spread map as a function of a plurality of posting pairs. Probable future prevalence and/or spread thereof may be determined by matching a function representing rates of spread over space and time to points and times of detection and/or a time series of previously and currently determined spread maps; such function may be used to estimate a future prevalence map at a later time. Such matching and/or function may be determined using machine-learning as described in this disclosure.

Still referring to FIG. 6, computing device may train a model as a function of the plurality of posting pairs, which model may be used to perform determinations and/or mapping as described above, and/or additional or alternative determinations and/or mapping. For instance, and without limitation, given a decentralized sensor network as described above that provides measurements over time and space, with probabilistic confidence, such data and/or network may be used to train a model to make a variety of predictions. Such predictions about a measured observable itself such as viral spread, air pollution or the like, or may include predictions about other variables, such as prevalence of asthma as predicted using prevalence of air pollution and/or respiratory illness. Different kinds of measurements may be fused, both to have more robustness against spurious reports and so that predictions can make use of richer data. Some potential techniques and applications may include predicting future sensor readings and/or test results, which may have several applications across a variety of domains. For instance and without limitation, time-series prediction models may operate on observations taken at k preceding time-steps (denoted $t_0, t_1, t_2, \ldots t_k$) and produce a prediction of the value observed at time step k+1 (denoted $t_{k+1}$). A variety of machine learning models such as a tong short-term memory (LSTM) model and/or a transformer model may be used. These models may take as input a fixed number of preceding observations to produce a prediction of a future observation. Machine learning models may also incorporate additional attributes including additional sensors or spatio-temporal information.

Model may include a machine-learning model. Machine-learning model, and training thereof, may be implemented in any manner described in this disclosure. Model may include a time-series prediction model as described above. Model may include a long short-term memory model and/or a transformer model.

Continuing to refer to FIG. 6, computing device may generate and/or output one or more data using model. Computing device may generate, using the model, a prevalence of an unsensed attribute as a function of the plurality of test results. An "unsensed attribute," as used in this disclosure, is an attribute that was not directly measured, but was predicted and/or estimated using one or more sensed values. A machine learning model used to predict sensor values for such a location may utilize existing attributes and/or features pertaining to a location, such as elevation, population density and/or any other potential sensor measurements and be trained on a data set sourced from the existing sensors and/or test results. Predicted values may be utilized as a surrogate for a measured value. This may represent an example of geographic value extrapolation. An example of a system that may perform in this manner may include, without limitation, a temperature sensor to measure ground temperature in an urban area: a prediction system may use attributes such as elevation, time of day, current month, and/or proximity to water bodies to predict the sensor reading. A model trained on a data set of such attributes and the associated readings may then be utilized to predict sensor readings of any area in the location without sensor coverage. A more general situation may incorporate a variety of other spatio-temporal information.

As a further non-limiting example, and still referring to FIG. 6, computing device may generate, using the model, an estimated prevalence at an unsensed region, defined as a region in which attributes were not directly measured. In a geographic setting with limited sensor coverage of a location, predictions may be used in unmonitored areas. A machine learning model used to predict sensor values for such a location may utilize existing attributes and/or features pertaining to the location, such as elevation, population density and any/or other potential sensor measurements, and be trained on a data set sourced from the existing sensors. Predicted values may then be utilized as a surrogate for the measured value; this may represent an example of geographic value extrapolation.]

In some embodiments, sensor readings and/or test results may be used by themselves for predictions using techniques such as Graph Label Propagation. For instance, if a particular location has no associated sensor reading, a discounted reading with appropriate sensor values may be computed from a nearby sensor or a weighted combination of nearby sensors. Methods such as Graph Label Propagation may exploit similarity structure inherent in a collection of sensors being used and may be utilized to (i) predict future sensor readings, (ii) compensate for unavailable sensor readings, or (iii) refine potentially noisy measurements. A collection of sensors and associated predictions, for instance using methods discussed above, may be utilized to compute error bounds on readings and make decisions about using these measurements in downstream applications. A technique may utilize a mixture of predictions, and multiple competing sensor measurements to evaluate quality of a particular sensor and/or measurement device.

Figure 7:
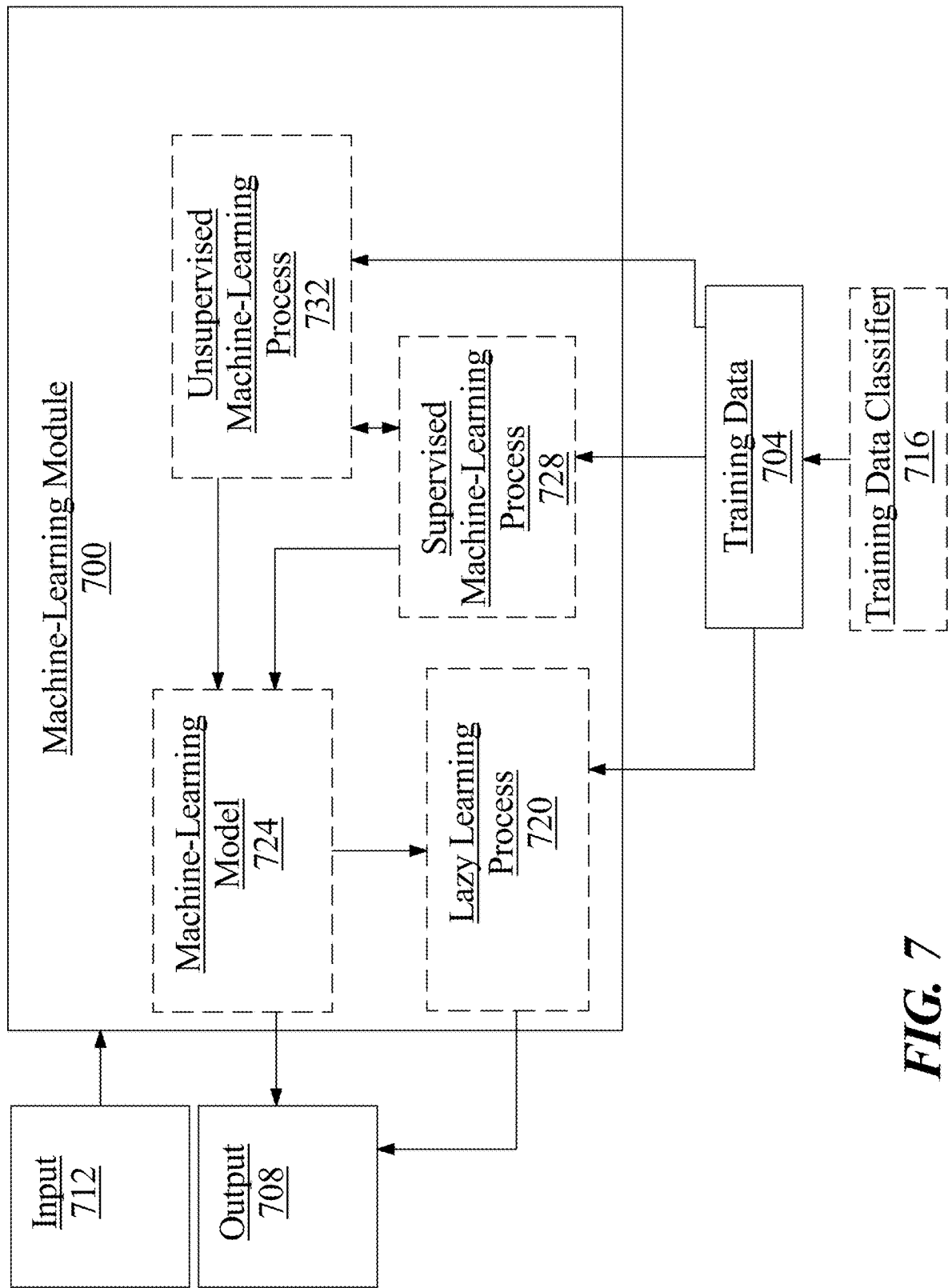
FIG. 7 is a block diagram illustrating an exemplary embodiment of a machine-learning module.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 8:
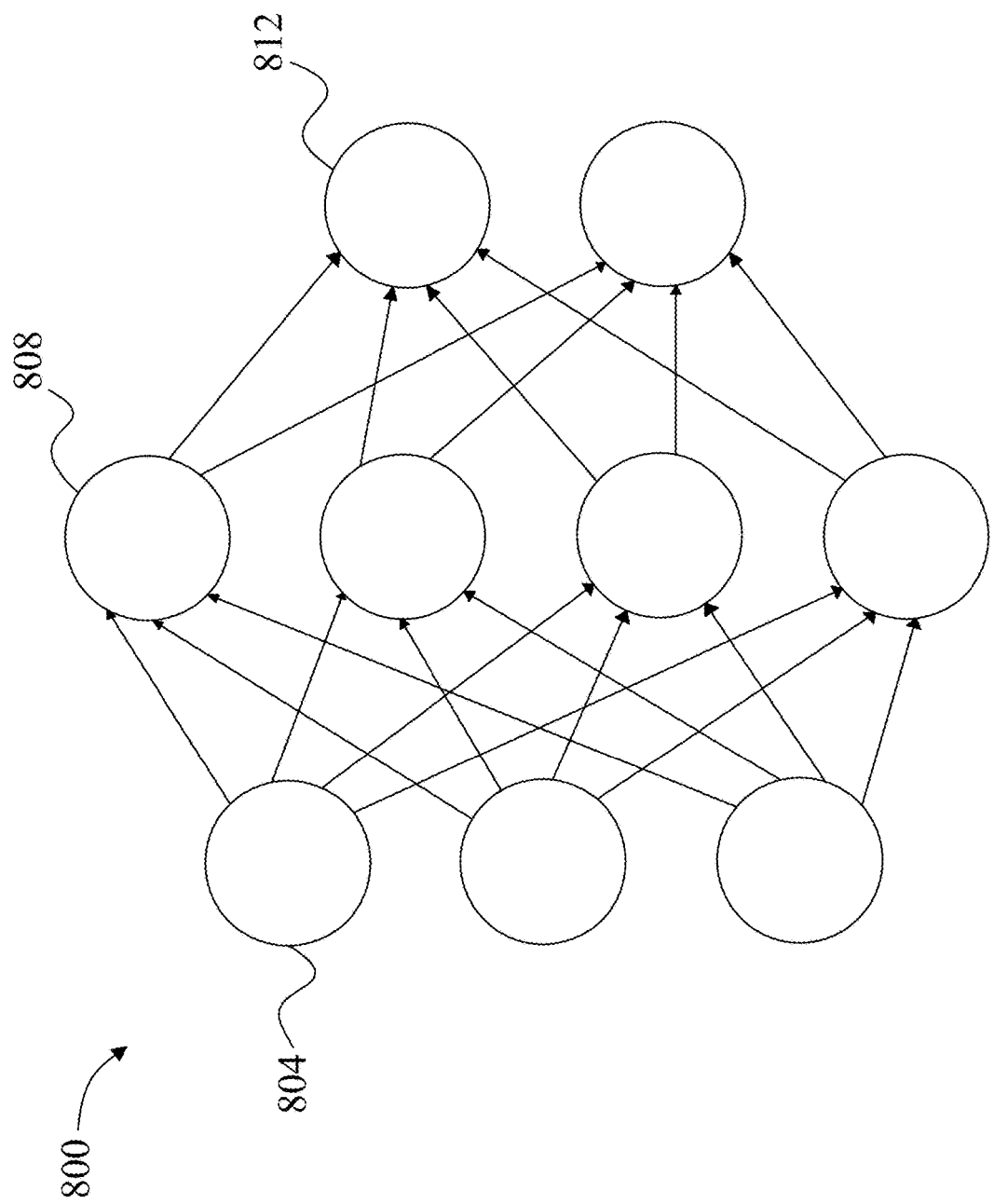
FIG. 8 is a schematic diagram illustrating an exemplary embodiment of a neural network.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 9:
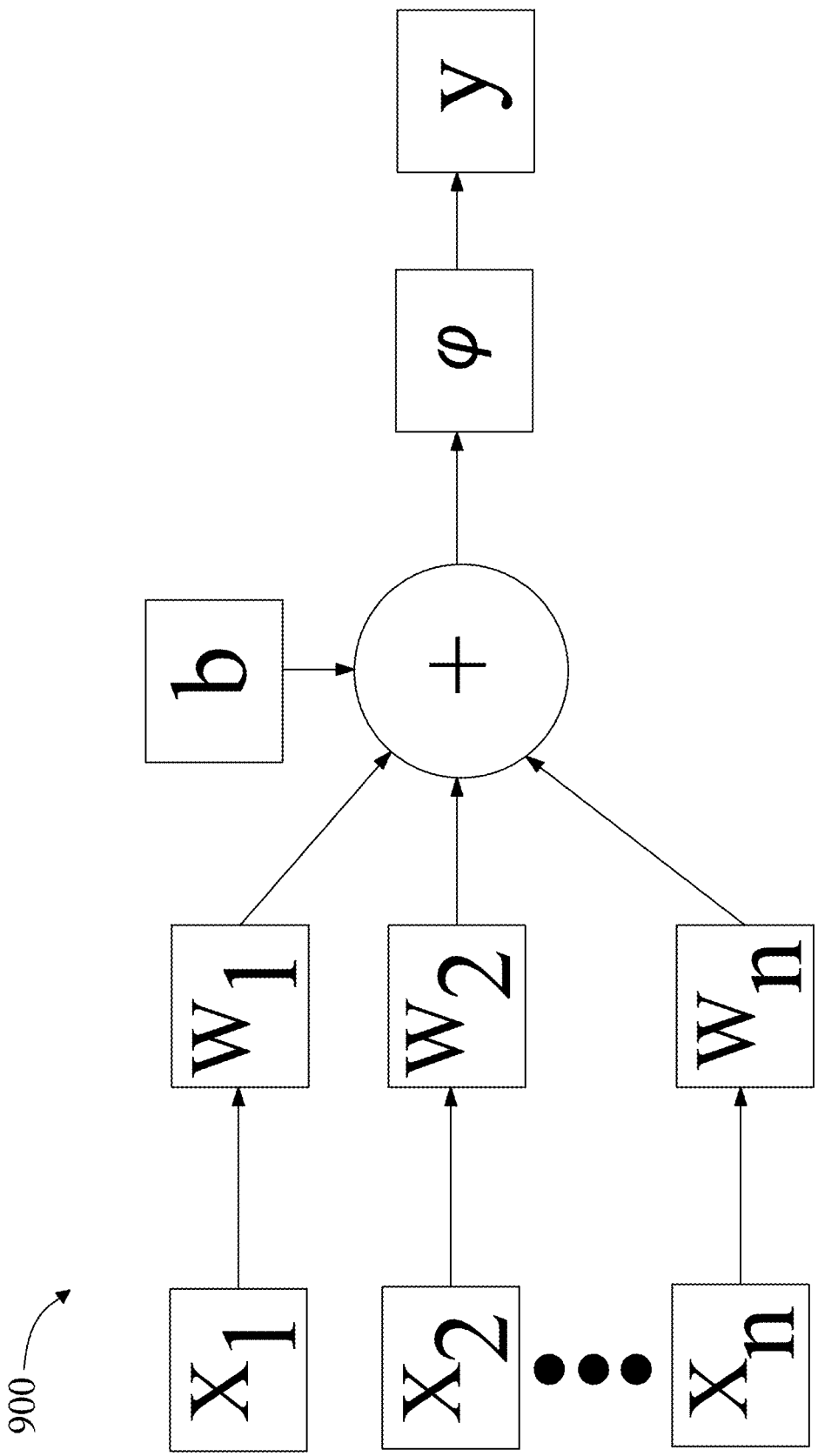
FIG. 9 is a schematic diagram illustrating an exemplary embodiment of a node in a neural network.

Referring now to FIG. 9, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
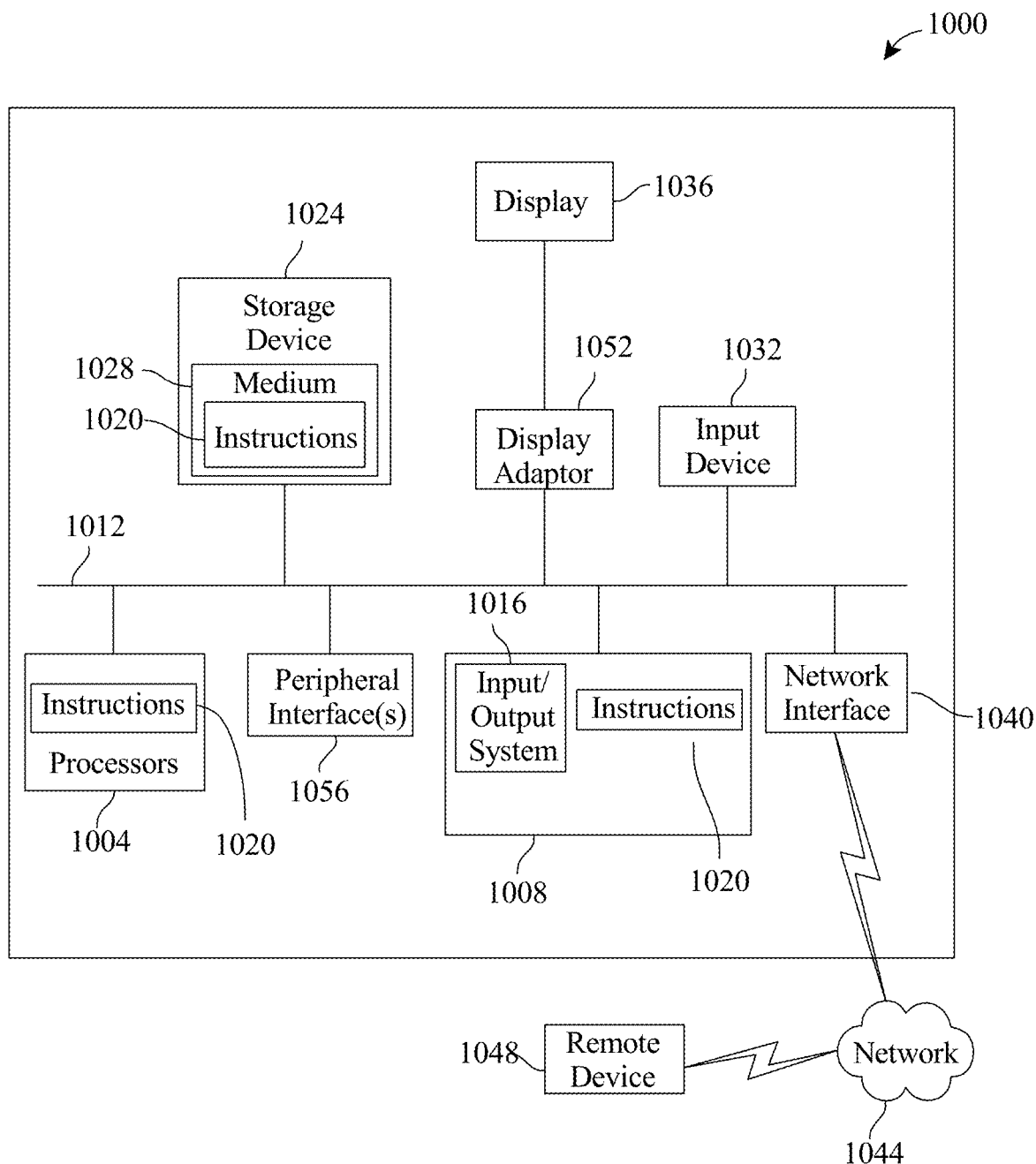
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC)

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alphanumeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of cryptographically secured medical testing, the method comprising:
   capturing, by a computing device, an unsealed test identifier corresponding to a test apparatus;
   generating, by the computing device, a cryptographic commitment to the unsealed test identifier;
   recording, by the computing device, a test result from the test apparatus;
   transmitting, by the computing device, to at least a local device a message including the test result;
   receiving, by the computing device, a digital signature on the message from the at least a local device; and
   generating, by the computing device, a record, the record including the digitally signed message and a secure proof of the cryptographic commitment.

2. The method of claim 1, wherein generating the cryptographic commitment further comprises posting the cryptographic commitment to an immutable sequential listing.

3. The method of claim 1, wherein the at least a local device further comprises a plurality of local devices.

4. The method of claim 1, wherein the message further comprises a location of the computing device.

5. The method of claim 1, wherein the message further comprises a timestamp and a location of the test apparatus.

6. The method of claim 1, wherein the message further comprises a value from a most recent state of an immutable sequential listing.

7. The method of claim 1, wherein the secure proof further comprises a zero-knowledge proof.

8. The method of claim 1, wherein the secure proof further comprises a one-out-of-many proof.

9. The method of claim 1, wherein the cryptographic commitment further comprises a cryptographic accumulator, and the proof of the cryptographic commitment further comprises a proof of membership in the cryptographic accumulator.

10. The method of claim 1 further comprising posting the record to an immutable sequential listing.

11. A non-transitory memory containing instructions configuring at least a processor to perform method steps for cryptographically secured medical testing, the method steps comprising:
    capturing an unsealed test identifier corresponding to a test apparatus;
    generating a cryptographic commitment to the unsealed test identifier;
    recording a test result from the test apparatus;
    transmitting to at least a local device a message including the test result;
    receiving a digital signature on the message from the at least a local device; and
    generating a record, the record including the digitally signed message and a secure proof of the cryptographic commitment.

12. The non-transitory memory of claim 11, wherein generating the cryptographic commitment further comprises posting the cryptographic commitment to an immutable sequential listing.

13. The non-transitory memory of claim 11, wherein the at least a local device further comprises a plurality of local devices.

14. The non-transitory memory of claim 11, wherein the message further comprises a location of the computing device.

15. The non-transitory memory of claim 11, wherein the message further comprises a timestamp and a location of the test apparatus.

16. The non-transitory memory of claim 11, wherein the message further comprises a value from a most recent state of an immutable sequential listing.

17. The non-transitory memory of claim 11, wherein the secure proof further comprises a zero-knowledge proof.

18. The non-transitory memory of claim 11, wherein the secure proof further comprises a one-out-of-many proof.

19. The non-transitory memory of claim 11, wherein the cryptographic commitment further comprises a cryptographic accumulator, and the proof of the cryptographic commitment further comprises a proof of membership in the cryptographic accumulator.

20. The non-transitory memory of claim 11 further comprising posting the record to an immutable sequential listing.

\* \* \* \* \*